United States Patent [19]
Anderson et al.

[11] Patent Number: 5,610,398
[45] Date of Patent: Mar. 11, 1997

[54] SYSTEM AND METHOD FOR IDENTIFYING AUTOMOTIVE AND COMMERCIAL REFRIGERANTS

[75] Inventors: J. Douglas Anderson; Stephen A. Morgan, both of West Chester; Chuck W. Montague, Glen Moore; Richard J. Nyce, Norristown, all of Pa.

[73] Assignee: Neutronics, Inc., Exton, Pa.

[21] Appl. No.: 401,205

[22] Filed: Mar. 9, 1995

[51] Int. Cl.⁶ ............................................. G01N 7/00
[52] U.S. Cl. .......................... 250/339.12; 250/339.13; 250/341.1; 250/343
[58] Field of Search .................... 250/339.12, 339.13, 250/341, 343

[56] References Cited

U.S. PATENT DOCUMENTS

| | | | |
|---|---|---|---|
| 4,858,460 | 8/1989 | Schohl et al. | 73/19 |
| 4,874,572 | 10/1989 | Nelson et al. | 250/339.13 |
| 4,914,709 | 4/1990 | Conlon et al. | 250/339.13 |
| 5,055,690 | 10/1991 | Bonne | 250/343 |
| 5,429,805 | 7/1995 | Uno et al. | 250/339.12 |
| 5,457,528 | 10/1995 | Tobias | 250/339.12 |

*Primary Examiner*—Michael J. Tokar
*Assistant Examiner*—Virgil O. Tyler
*Attorney, Agent, or Firm*—Ratner & Prestia

[57] ABSTRACT

A system and method for determining the presence of multiple vapor gases in a refrigerant sample. An infrared light source illuminates a refrigerant sample located in a test area between the light source and a plurality of infrared detectors. Each of the infrared detectors is sensitive to a different predetermined wavelength range of infrared light, with each of the detectors outputting a separate electrical signal corresponding to the infrared light received in its respective wavelength range. A processor then reads the output electrical signals and determines whether the electrical output signals correspond to a particular refrigerant and displays the result of the determination on a display.

16 Claims, 20 Drawing Sheets

138
(CON'T)

R12_WEIGHT=(R12_MOLE_CONC*R12_GRAMS_PER_MOLE)=10332.59g
R22_WEIGHT=(R22_MOLE_CONC*R22_GRAMS_PER_MOLE)=11.15g

⇓

*CALC. TOTAL WEIGHT:*
WEIGHT_TOTAL=(AIR_WEIGHT+R134_WEIGHT+R12_WEIGHT+R22_WEIGHT)=10843.45g

⇓

*CALC. PERCENT CONCENTRATION FOR EACH GAS:*
AIR_WEIGHT_PER=(100*AIR_WEIGHT/WEIGHT_TOTAL)=3.72%
R134_PER=(100*R134_WEIGHT/WEIGHT_TOTAL)=0.889%
R12_PER=100*R12_WEIGHT/WEIGHT_TOTAL)=95.29%
R22_PER=(100*R22_WEIGHT/WEIGHT_TOTAL)=0.103%

⇓

*REJECT CONCENTRATION LESS THAN 0.5%:*
SETR22_WEIGHT=0

⇓

*AIR WEIGHT CONCENTRATION:*
IS LESS THEN 70% DO NOT FAIL DUE TO HIGH AIR CONCENTRATION

⇓

*REMOVE AIR_WEIGHT FROM WEIGHT_TOTAL & USE NEW R22_WEIGHT:*
WEIGHT_TOTAL=(WEIGHT_TOTAL-AIR_WEIGHT)=10428.98g

⇓

*RECALC. PERCENT CONCENTRATION FOR EACH GAS:*
R134_PER=(100*R134_WEIGHT/WEIGHT_TOTAL)=0.924%
R12_PER(100*R12_WEIGHT/WEIGHT_TOTAL)=99.076%
R22_PER=(100*R22_WEIGHT/WEIGHT_TOTAL)=0.000%

⇓

*RESULT:*
R12_PER>=98.0%
SAMPLE LED OFF, R12 LED ON
SCROLLING DISPLAY OF:
R12 - 99.1

140

R134 - 0.9

⇓

WHEN MODE SWITCH IS PRESSED: AIR CAL.

SYSTEM AND METHOD FOR IDENTIFYING AUTOMOTIVE AND COMMERCIAL REFRIGERANTS

FIELD OF THE INVENTION

The present invention relates to a system and method for identifying refrigerants. More specifically, the present invention relates to the identification of particular automotive and commercial refrigerants using infrared spectroscopy.

BACKGROUND OF THE INVENTION

It has been suggested that certain fluorocarbons which have commonly been used in refrigerants can damage the ozone layer when released into the atmosphere. This suggestion has led to the replacement of these damaging fluorocarbon refrigerants with non-ozone damaging fluorocarbons. As the ozone damaging fluorocarbons are removed and new non-damaging fluorocarbons are used, it becomes important to be able to identify and keep segregated the various types of refrigerants. Increased government regulation of the fluorocarbons in the United States adds to the responsibility of the refrigerant service facilities, such as automotive repair facilities, which handle refrigerants.

In the automotive field, refrigerants known as R12, R22, R134A and various hydrocarbon blends (such as OZ12 and OZ12A) have been used for automotive air conditioning refrigerants. Of these four refrigerants, R134A, OZ12, and OZ12A are the least ozone damaging refrigerants which are presently being used in automobiles. However, OZ12 and OZ12A can be explosive under certain conditions and are now considered undesirable for automotive refrigeration applications. Older cars may still be using R12 as a refrigerant. Because of the cost involved in converting existing automotive hardware to handle R134A, existing automobile owners may elect to continue using their prior refrigerant. Because of government regulation, however, R12 will no longer be manufactured after 1995.

R22 is a home air conditioning refrigerant which has been used, illegally, as a replacement for R12, because of its lower cost. R22 is not appropriate for use as an automobile refrigerant due to elastomer material incompatibility and higher vapor pressure of operation.

The various hydrocarbon blends are combustible and are no longer used as an automotive refrigerant.

It is possible in an automobile's refrigerant system, as well as in the storage tanks of a refrigerant service center or auto service center, that a mixing of the above refrigerants can take place. Because of the dangers associated with certain of the automotive refrigerants, as well as increasing government regulation regarding which refrigerants can be used, it is desirable to identify the individual refrigerant gases in both automotive systems and storage facilities in order to maintain separate and pure stores of these gases. If a storage tank of refrigerant gases is contaminated, it should not be used for refilling an automotive refrigerant system.

In commercial air conditioning/refrigeration installations, there are approximately 25–35 different commercial refrigerants which are commonly used. As in the case of the automotive refrigerants, certain commercial refrigerants are also ozone damaging. In addition, certain commercial refrigerants may be incompatible with a system designed for another commercial refrigerant. Because of the wide variety of refrigerants utilized in the field, it is possible that more than one refrigerant is inadvertently present in a particular commercial refrigeration system and/or refrigerant storage tank. Thus, it is desirable for commercial refrigerant systems to be able to identify all refrigerants present in the system.

Current products used for refrigerant identification have shortcomings and have not been met with a great deal of industry acceptance. Robinaire manufactures a device which uses thermal conductivity to measure R12 contained in R134A refrigerant supplies. This technology does not detect or account for air contained in the sample in its analysis. Carrier manufactures a device using chemical analysis, and is limited to detecting only a single refrigerant (R134A) and can not detect R22. Liebold Inficon uses acoustic technology and does not detect or account for air contained in the sample.

One method which has been used to identify gases is infrared spectroscopy. Most gases absorb infrared energy at specific wave lengths in the spectrum and, in many cases, at multiple points in the infrared spectrum. Infrared spectroscopy has been used to observe the phenomenon and identify particular gases. Traditional infrared spectroscopy equipment and methods, however, are not practical for field use at installations such as a local automotive repair facility because of cost, size, and robustness. Existing infrared spectroscopy units, designed for laboratory use, are inappropriate for rigorous "unclean" environments such as that found in a local automotive repair facility. They also fail to meet the requirements of a portable device for transport and operation at a particular commercial establishments having commercial refrigerant systems.

Tiff has manufactured a device using infrared analysis for detecting a single refrigerant, R12, using a single infrared detector. This device, too, does not detect and account for air which may be present in the sample. Accordingly, the accuracy for R12 analysis using the Tiff device is questionable if air is present in a sample.

SUMMARY OF THE INVENTION

The present invention comprises a system and method for determining the presence of multiple vapor gases in a refrigerant sample. An infrared light source is used to illuminate a refrigerant sample which has been input into a test area. The test area is physically located between the infrared light source and a plurality of infrared detectors. The infrared detectors receive infrared light after it passes through the refrigerant sample. Each of the infrared detectors is sensitive to a different predetermined wavelength range of infrared light. Each of the infrared detectors is adapted to output a separate electrical signal corresponding to the infrared light received in its respective wavelength range.

Once a refrigerant sample is illuminated by an infrared light source and the plurality of infrared detectors receives infrared light passing through the refrigerant sample, and the resultant electrical signals are amplified and filtered, a processor reads the output electrical signals and determines whether the electrical output signals correspond to a particular refrigerant. The results of this determination are then displayed on an output device.

BRIEF DESCRIPTION OF THE FIGURES

The invention will be described by way of non-limiting example, with reference to the attached drawings in which:

FIGS. 12A and 12B are flow diagrams illustrating an example operation of an exemplary refrigerant identification system;

DETAILED DESCRIPTION OF THE INVENTION

Figure 1:
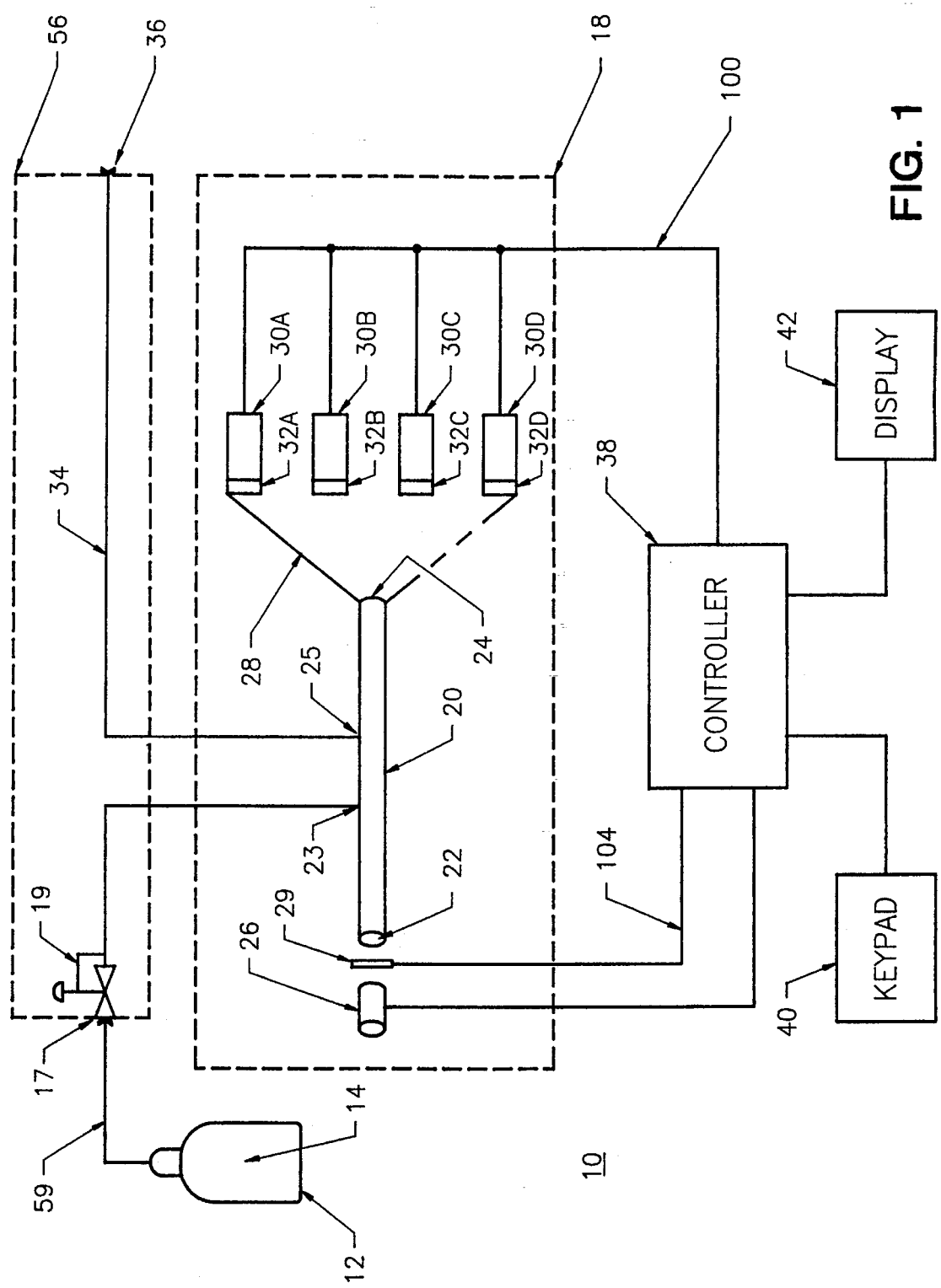
FIG. 1 is a schematic block diagram of an exemplary refrigerant identification system.

There is shown in FIGS. 1–4, an exemplary refrigerant gas identifier system 10 and its various components. There is shown in FIG. 1 a schematic block diagram of refrigerant identifier system 10. System 10 corresponds to model RI-2002P portable automotive refrigerant identifier, part no. 7-08-1000-00-0, made by Applicants' Assignee, Neutronics, Inc. System 10 is used for the identification of vapor gases or refrigerant gases which comprise or contaminate a refrigerant. In an exemplary embodiment, system 10 is used to identify automotive refrigerants. In an additional embodiment, system 10 is used to identify commercial refrigerants.

In FIG. 1, a refrigerant 14 is shown contained within a cylinder 12. Cylinder 12 is connected to an input port 17 through a hose 59. The input port 17 then connects the hose 59 and cylinder 12 to the pressure regulator 19. Although shown and contained in cylinder 12, refrigerant 14 can be contained in an automobile's refrigerant system, or other containment means with a direct connection to system 10 for testing.

Refrigerant vapor 14 passes through plumbing system 56 (shown in FIG. 3) into optical bench 18. Optical bench 18 uses non-dispersive infrared technology (NDIR) and is manufactured by Janos Technology, Inc. of Townsend Vermont for Applicant under part no. 4082-3001. Janos Technology, Inc. also manufactures similar optical benches for part per million (PPM) analysis of trace gases. Optical bench 18 contains an infrared light source 26, a sample cell 20 having a first end 22 and a second end 24. Infrared light from infrared light source 26, is interrupted at a constant rate by chopper 29, before entering sample cell 20. Infrared light having passed through refrigerant sample 14 contained in sample cell 20 exits sample cell 20 through second end 24. In a preferred embodiment, sample cell 20 is an aluminum cylinder three millimeters in length. First end 22 and second end 24 are closed and sealed with glass windows. Refrigerant 14 enters sample cell 20 at port 23 and exits cell 20 at port 25. After exiting sample cell 20, refrigerant 14 travels through hose 34 and is vented at outlet port 36.

Optical bench 18 also contains a plurality of infrared detectors. In an exemplary embodiment, four infrared detectors 30A–30D are used and illustrated in FIG. 1. In an exemplary embodiment, Model 407 Thermally Compensated Pyroelectric IR Detectors manufactured by Eltec Instruments, Inc. of Daytona Beach, Fla. are used. These detectors operate in the mid and far band infrared wavelengths. In other embodiments, two or more detectors could be used, depending upon the number of separate refrigerants being detected and the physical requirements of optical bench 18. The number of separate detectors can correspond to the possible number of separate refrigerants being analyzed.

Each of the infrared detectors has a filter designed to filter out all but a predetermined wavelength range of infrared light. The particular wavelength range of infrared light for each filter corresponds to a wavelength range which encompasses the predominant infrared light wavelength for a particular refrigerant gas after illumination (excitation) of the refrigerant gases by infrared light source 26. In an exemplary embodiment, four separate infrared filters 32A–32D are shown positioned on a corresponding detector 30A–30D. Infrared filters 32A–32D are coated glass filters, designed to pass light of a particular wavelength range. In an exemplary embodiment, a separate one of filters 32A–32D is designed to filter out all wavelengths except those in its specified ranges, namely 3.14 microns (hydrocarbons), 10.3 microns (R134A), 11.3 microns (R12), and 12.5 microns (R22). In this way, each detector/filter combination is sensitive to a different predetermined wavelength, corresponding to a particular refrigerant. Being sensitive to the wavelength of light absorbed by a particular filter, a detector can output a signal based on its detection/lack of detection of a particular wavelength. Each detector is designed to respond in a discrete part of the infrared spectrum where each refrigerant and hydrocarbon has a maximum absorbance, and also, to provide minimum cross-sensitivity from the other refrigerants. After illumination by infrared light source 26, non-absorbed infrared light leaves sample cell 20 through second end 24 in a dispersion path 28 which provides that equal amounts of non-absorbed infrared light are received by each of the infrared detectors 30A–30D, normal to each of the infrared detectors 30A–30D. Dispersion path 28 is arrived at according to the internal geometry of optical bench 18 in an exemplary embodiment.

Infrared light source 26 is controlled by a controller 38 which in an exemplary embodiment is a microprocessor with supporting circuitry and logic. Infrared light source 26 is also interrupted by mechanical chopper 29 which is oscillated by controller 38. Controller 38 also receives output signals from infrared detectors 30A–30D. The output signals from infrared detectors 30A–30D have an amplitude component corresponding to the amount of infrared light radiation which is received by a respective detector 30A–30D. The greater the amount of infrared light radiation received, the higher the amplitude and thus the stronger the electrical signal output by a particular infrared detector. The output of each infrared detector thus corresponds to the presence of a particular refrigerant gas and the amount of a particular refrigerant gas. Controller 38 receives/reads electrical signals from the infrared detectors and determines which, if any, refrigerant gas has been detected. Controller 38 may also determine the amount of the detected refrigerant. The results of the determination are output to a display panel 42.

A key pad 40 is also shown connected to controller 38. Key pad 40 allows an operator to start a test or turn off an alert horn, in an exemplary embodiment of the present invention.

Figure 2:
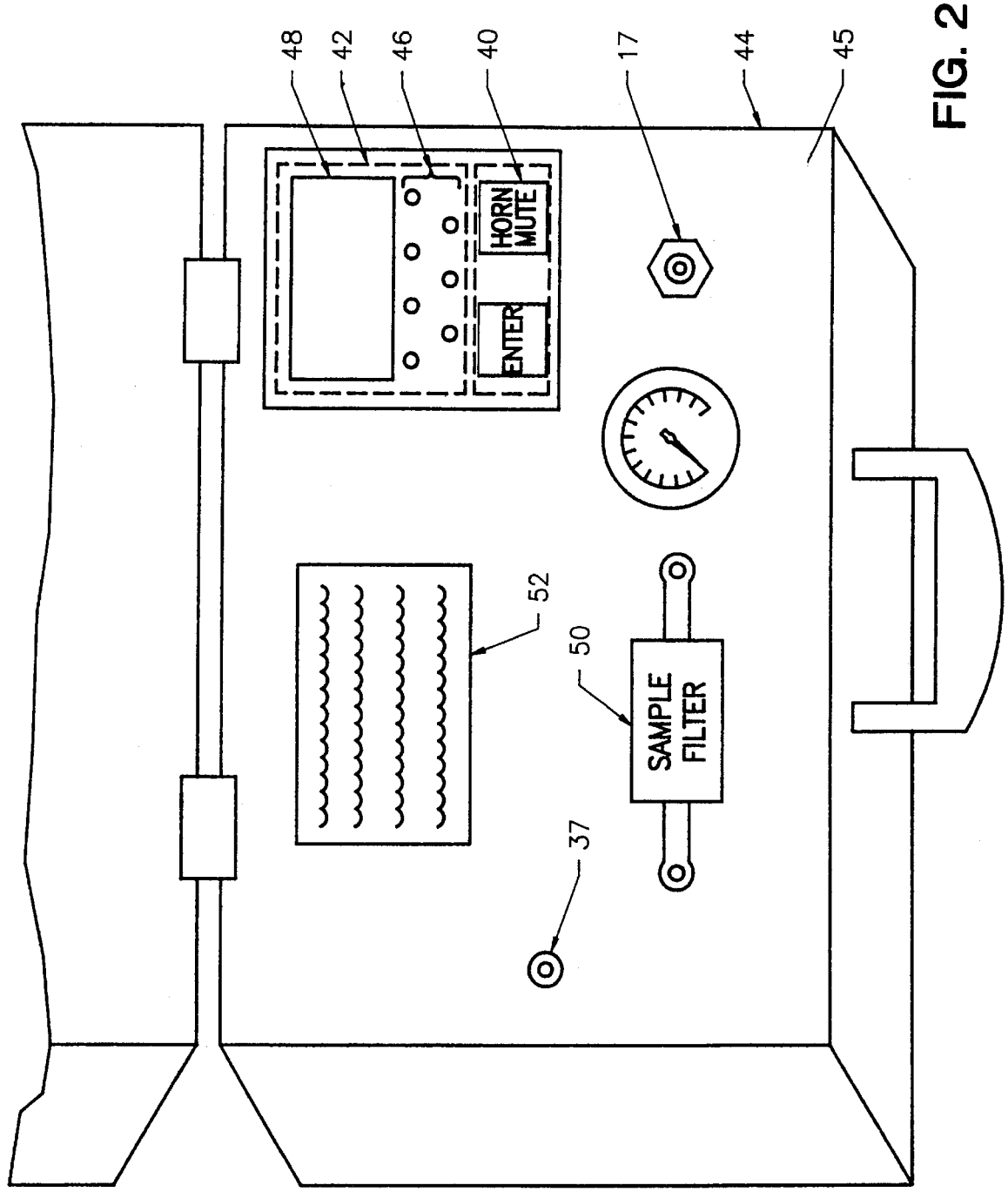
FIG. 2 is a perspective view of a case containing an exemplary refrigerant identification system showing input, output, display and controls.

System 10 can also identify and account for air which may be present in a refrigerant sample. Although the major components of air have no infrared spectral absorbance, they can act as a dilutant. Thus, air which is present in a refrigerant sample will proportionately reduce the response level at each infrared detectors 30A–30D. In order to account for air, system 10 measures the volumetric gas concentration of the aforementioned refrigerant/hydrocarbon. By adding up the concentrations of these components, the difference between this total and 100% is considered air and subtracted out from the total. The volume percentages of the respective refrigerants, air, and hydrocarbons are then converted to a weight percent purity to determine a true refrigerant percentage of the refrigerant sample. There is shown in FIG. 2 an operator panel contained in a case 44. In an exemplary embodiment, system 10 is designed to be a self-contained portable unit, contained in case 44.

Operator panel 45 shows an LCD text display 48 in an output display area 42 for providing operator cues during operation, as well as output information concerning any refrigerants, and percentages of refrigerants, air, and hydrocarbons detected. Output display area 42 also contains a plurality of LEDs 46 which, in an exemplary embodiment, are used to indicate which particular automotive refrigerant is detected, as well as system status. Keypad 40 is shown with two buttons: an enter button and a mute button. The mute button is used to turn off an alert horn. It will be understood that other types of keypads can be incorporated, allowing additional operator information or customization such as to identify a particular automobile's registration no. or account no. for archival purposes. An instruction legend 52 is also present on an exemplary embodiment to assist the operator in operation of system 10.

An inlet port 17 connects system 10 to a refrigerant gas supply being tested. System pressure gauge 54 is used to convey regulated refrigerant gas pressure to indicate presence of sample refrigerant 14. Sample filter 50 is used to filter out oils and particulates from a refrigerant sample 14 before it enters optical bench 18. In this location, sample filter 50 is easily replaceable by an operator. An air intake port 37 is also shown. Air intake port 37 is used to allow entry of air used for purging a previous sample, prior to a new refrigerant sample test.

Figure 3:
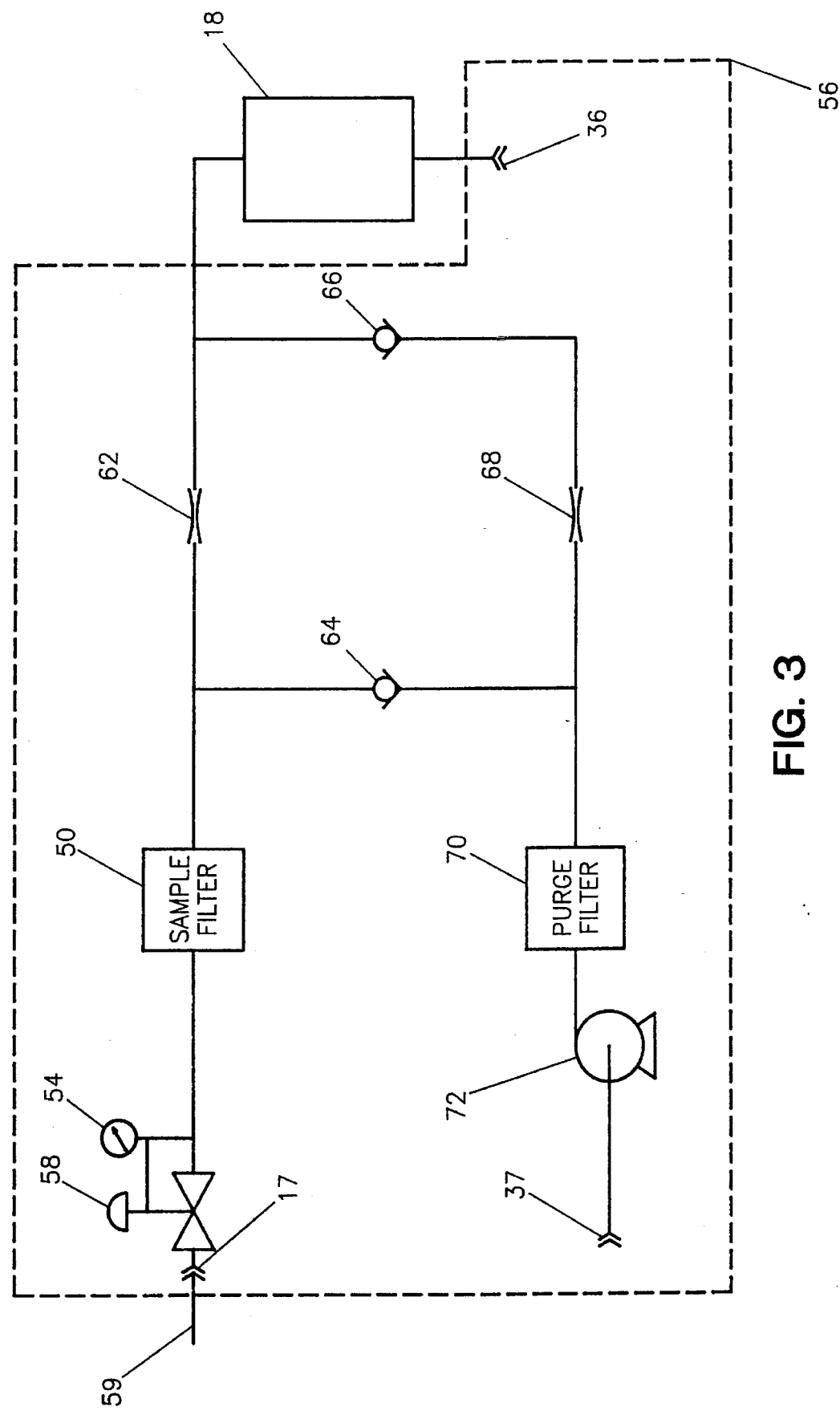
FIG. 3 is a schematic drawing of the plumbing of an exemplary refrigerant identification system.

There is shown in FIG. 3 a schematic diagram of plumbing system 56 for system 10. In an exemplary embodiment, plumbing system 56 is also contained in case 44 shown in FIG. 2. Plumbing system 56 is the passage way for refrigerant sample 14, as well as for air during an air purge. Refrigerant sample 14 enters plumbing system 56 through sample hose 59 and inlet port 17. Refrigerant sample 14 is then regulated to low pressure by pressure regulator 58. Pressure within plumbing 56 is monitored by pressure gauge 54. A refrigerant sample first passes through sample filter 50 where oils and particulates are filtered out. At sample orifice 62, refrigerant sample flow and pressure is reduced to allow a measured amount of flow of refrigerant sample 14 to enter optical bench 18. Check valves 64 and 66 prevent flow of refrigerant sample 14, except into optical bench 18. Following testing in optical bench 18, refrigerant sample 14 exits via outlet 36.

Prior to a refrigerant sample test, plumbing system 56 is purged with air to remove any prior sample and/or contaminants. Air is input through inlet port 37 with the assistance of pump 72. Inlet air passes through purge filter 70 to remove any particulates prior to purging. Air passes through purge orifice 68 where air flow is reduced to a flow level appropriate for optical bench 18 and to divide purge flow. Air passes through check valve 66 and then through optical bench 18 and out outlet port 36. Sample orifice 62 acts as a barrier, preventing air flow from circulating back. This results in all air flow through this path going through optical bench 18. Purge air also passes through check valve 64 and out through sample filter 50, regulator 58, inlet port 17, and hose 59. Sample orifice 62, although allowing a small amount of purge air to pass, prevents the majority of purge air from passing so that it effectively purges the front end of plumbing system 56 and exits through hose 59.

Figure 4:
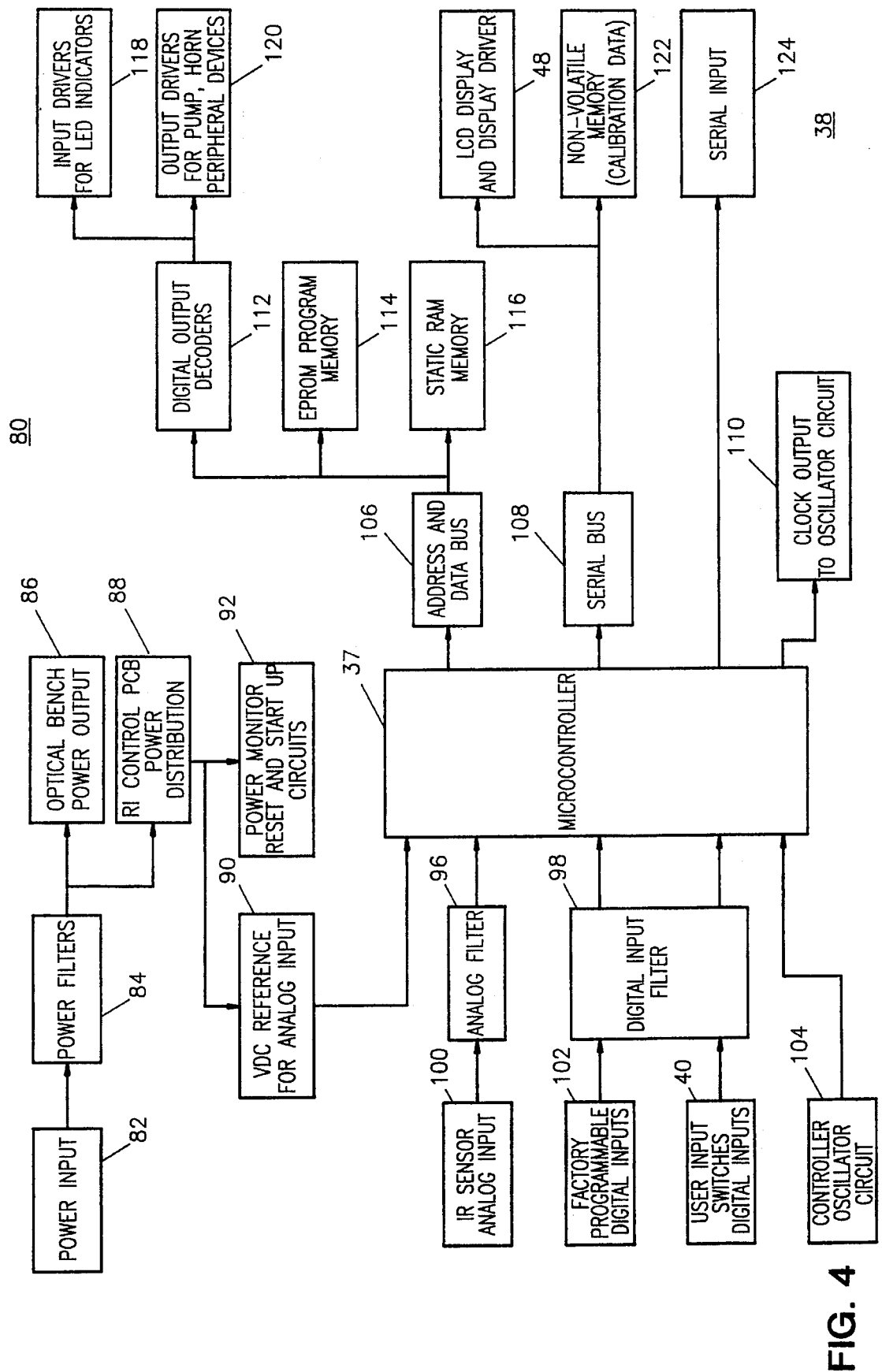
FIG. 4 is schematic block diagram of the electrical/logic connections of an exemplary refrigerant identification system.

There shown in FIG. 4 a block schematic diagram of controller 38 illustrating the electrical and logic circuitry for system 10. In an exemplary embodiment, a 20–40 watt power supply 82 is used to provide the required DC Voltages. Power filters 84 are resistor capacitor networks which are used to prevent power fluctuations and interference. Optical bench power output 86 provides output for the various components used in optical bench 18, such as infrared light source 26, an oscillator clock circuit, an oscillator and various analog circuitry. Refrigerant identifier control printed circuit board power distribution connections 88 provide power for other integrated circuits and peripheral devices such as display 42 and alert horn (not shown). DC voltage reference 90 sets the full scale range of the analog to digital convertor (ADC) at 2.5 volts. Power monitor and reset start-up circuits 92 are used to shut down processor 38 if power drops below operating voltages. This would prevent data processing errors from low power. It also provides a delay to allow processor 38 to be at full power before executing any instructions. This too prevents data processing errors.

Infrared sensor input 100 comprises the inputs from infrared detectors. In an exemplary embodiment, there are four infrared detectors 30A–30D which provide input signals. In an exemplary embodiment, the input signals are analog signals having a 0–2.5 volt peak to peak amplitude at 3 Hz, with an offset of 1.25 volts. Analog filters 96 are resistor capacitor networks which reduce high frequency interference to the infrared detector inputs from the power supply and/or microprocessor 38. Factory programmable digital inputs 102 allow a manufacturer to configure the control printed circuit board for predetermined options. Example options are factory auto calibration and user configurations. User input switches 40 are control signals provided by an operator. In an exemplary embodiment, these are the enter switch and horn mute switch. Data input filter 98 prevents high frequency interference from causing input signal errors.

Controller oscillator circuit 104 is the processor clock for microprocessor 38. In an exemplary embodiment, oscillator circuit 104 operates at 11.0592 MHz. Controller 38 includes a microprocessor 37 which controls the operation of system 10. In an exemplary embodiment, the 80C552 microprocessor by Phillips Semiconductor is used. Microprocessor 37 uses address and data bus 106 for both external memory access and digital output. Address and data bus 106 is connected to digital output decoders 112 which interprets the unique address for the LED indicators and peripheral devices. This in turn allows control output drivers 118 which power selected LED indicators 46. Output drivers 120 provide power for pump 70 and alert horn (not shown). Additional peripheral devices may also be connected here for operating system 10 with microprocessor 37. Static RAM memory 116 is used for storage of variables and resultants during calculations by microprocessor 38.

Serial bus 108 is an IIC serial bus for carrying serial bus signals from microprocessor 38. LCD display driver 48 and EEPROM memory 122 are connected to serial bus 108. Additionally, external devices such as a serial port (not shown) for a computer printer or modem can be connected to serial bus 108. Each of these devices has a unique address. EEPROM 122 contains calibration data. This memory is retained even after power is shut off for system 10. Serial output 124 allows microprocessor 38 to communicate with an external computer or printer. Microprocessor 38 contains a Universal Asynchronous Receiver Transmitter (UART) which communicates through serial output 124. Clock output 110 sends a three KHz signal to the oscillator circuit in optical bench 18. This signal is divided down to produce a 3 Hz signal required at the analog input of optical bench 18.

FIGS. 15A, 15B, 15C and 15D show example mole percentage vs. dB output curves. Each curve defines an acceptable envelope for the performance of a specific detector used in optical bench 18. Each curve defines four dB ranges for a specific mole percentage of refrigerant gas being tested (namely, 10%, 50%, 98% and 100%, for an exemplary embodiment). During manufacturing, a curve within the range depicted in FIGS. 15A–15D is used to calibrate each detector 30A–30B in system 10. Appropriate calibration information is stored in EEPROM 122 during manufacturing. ps Automotive Refrigerant Gas Identifier There shown in FIG. 5 a flow chart 130 showing the main operation process of the present invention. Operation of system 10 begins with initialization of controller 38 in block 132. Next, a warm-up/air calibration takes place which allows optical bench 18 to reach minimum operating temperature, clears optical bench 18 of residual refrigerant gases, and clears plumbing 56 of residual refrigerant gases in block 134. Following calibration, a refrigerant sample is loaded into system 10, through plumbing system 56 by attaching hose 16 to a refrigerant sample source. In block 138, the identification of a refrigerant sample 14 takes place. Identification involves the steps of receiving/reading the output information from detectors 30A–30D, interpreting the data to identify the type of refrigerant gas and displaying the results. In block 140 system 10 is purged with air and recalibrated. Finally, in block 142 a new sample can be input.

Figure 5:
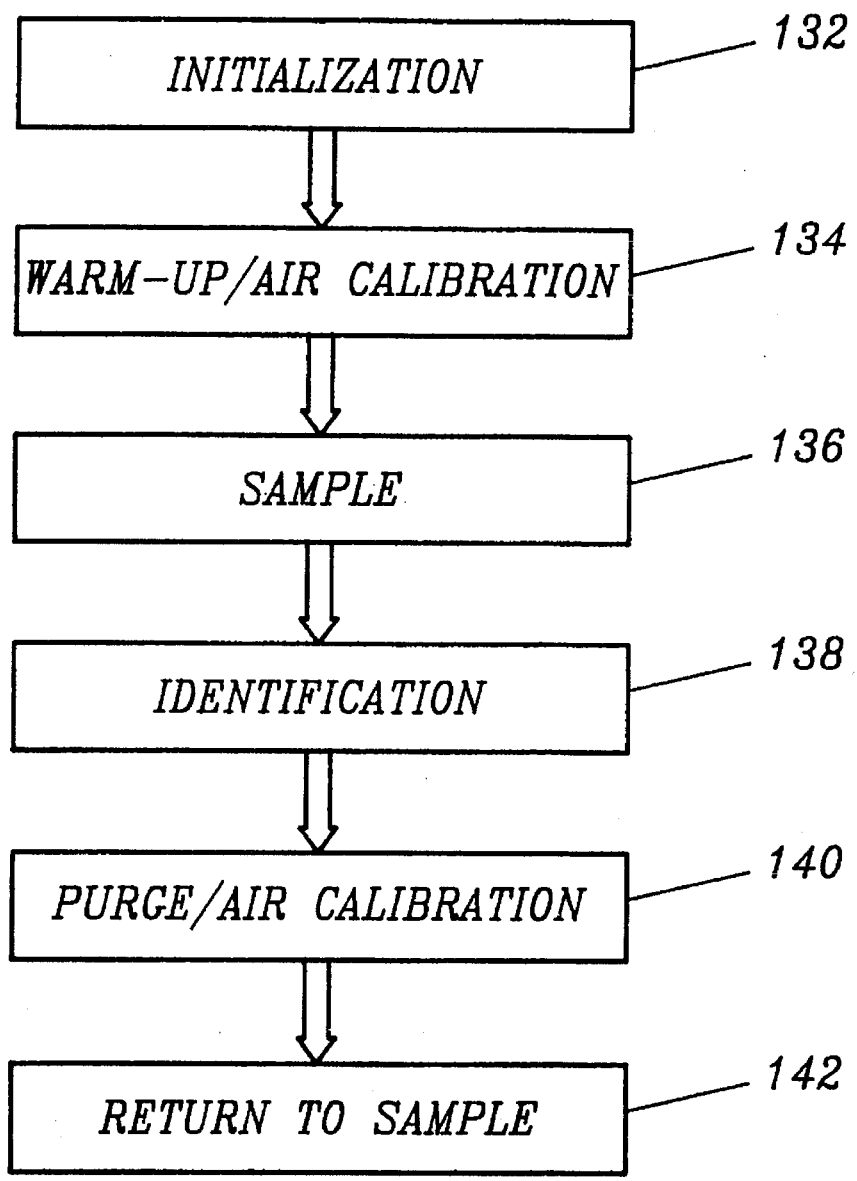
FIG. 5 is a flow chart of the main operation process of the exemplary refrigerant identification system.

FIGS. 6–11 expand upon the process steps shown in FIG. 5.

Figure 6:
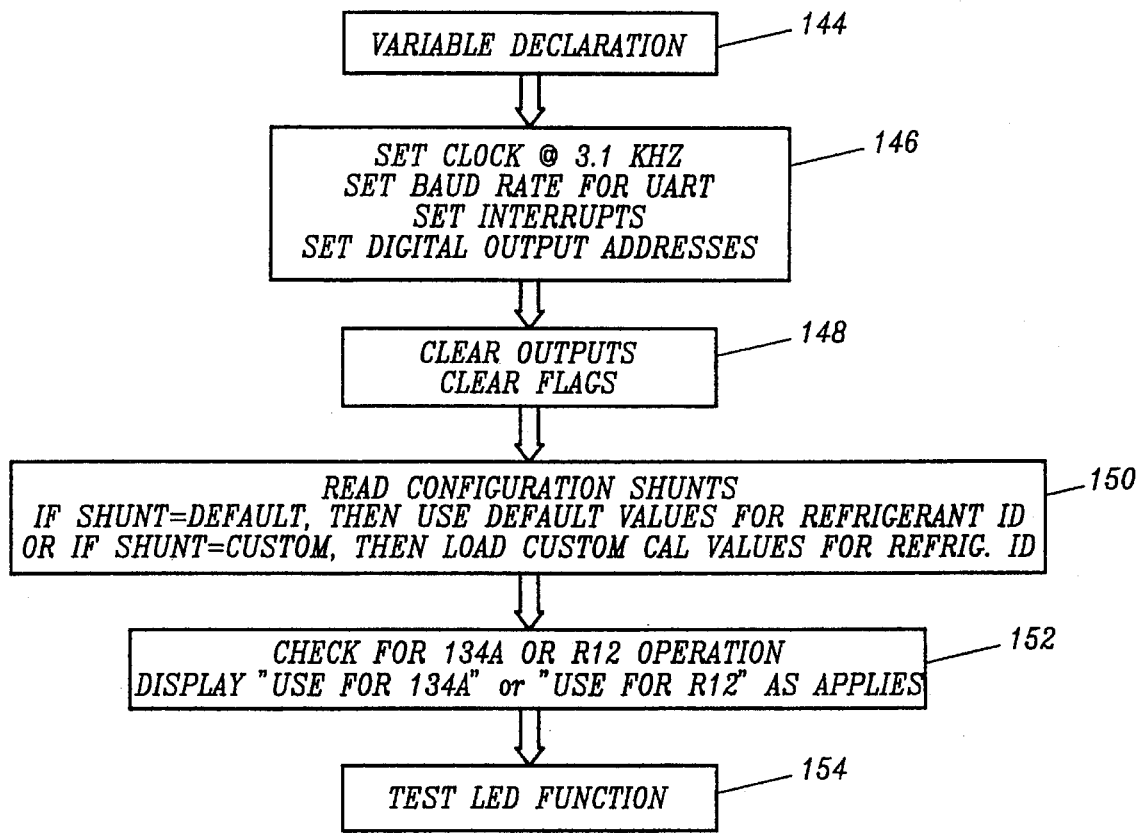
FIGS. 6–10 are expanded flow charts of the various processes illustrated in FIG. 5.

There is shown in FIG. 6 a flow chart showing the steps involved in initialization process 132. Initialization begins by a variable declaration in block 144. Variable declaration initializes variables to their default values, such as LED addresses and time outs. In block 146, the oscillator clock is set at 3.1 KHz to ensure proper timing. The baud rate for the UART, which is a part of controller 38, as well as interrupts for the digital output addresses are also set. Information for these settings is stored in EEPROM 122 (FIG. 4). In block 150, configuration shunts are read to determine whether the integral defaults for particular refrigerant identification are used, or whether a set of custom calibration values are to be used for refrigerant identification. If custom calibration values are used, they are entered through block 102 (FIG. 4). Custom calibration values can include calibration curve identification numbers (i.e. curves shown in FIG. 15A–15D); an optical bench 18 serial number and a hydrocarbon alarm set point. In block 152, a test is made to determine whether option is set for R134A only R12 only, or both. In an exemplary embodiment, system 10 can detect four separate refrigerants. For dedicated applications, system 10 can be restricted to detect only R134A or R12 or combinations of refrigerants, i.e. R134A and R12. Operation restriction can be set by the operator. In block 154 LEDs 46 are tested to ensure proper operation.

Figure 7:
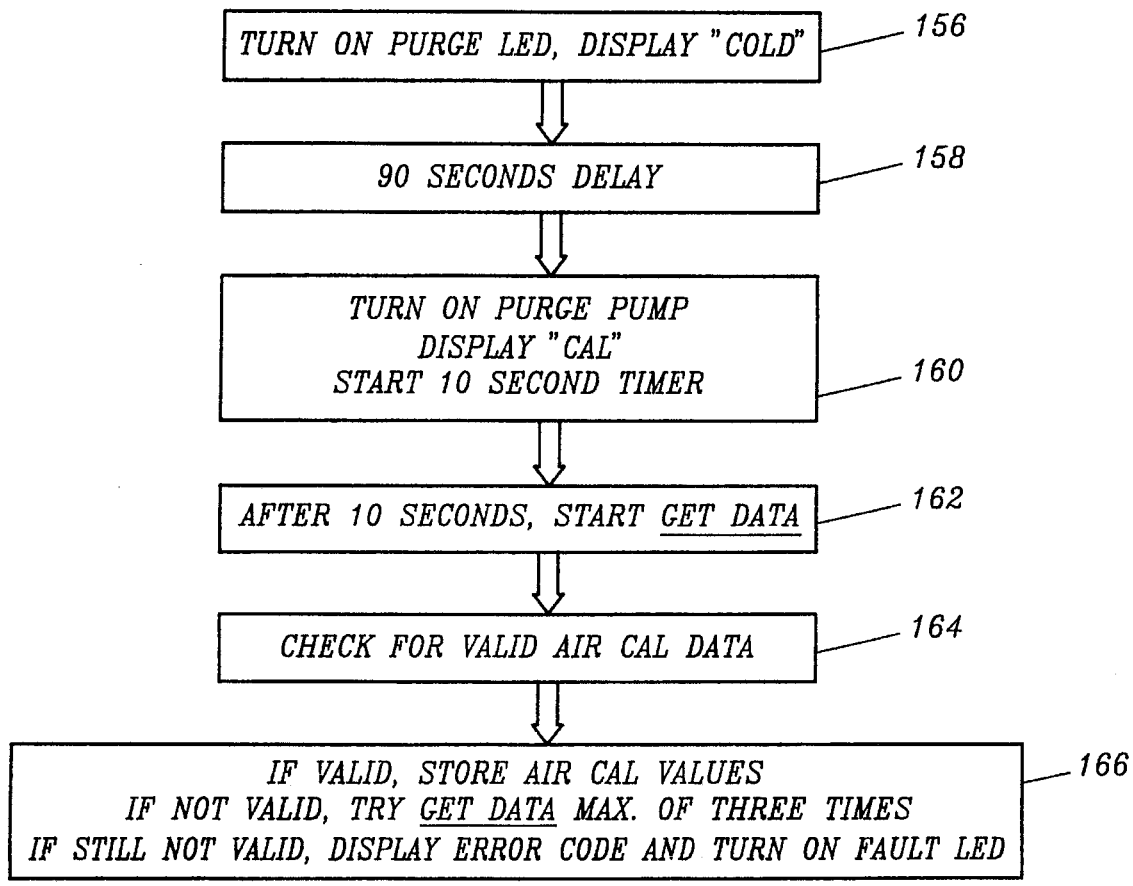
Figure 11:
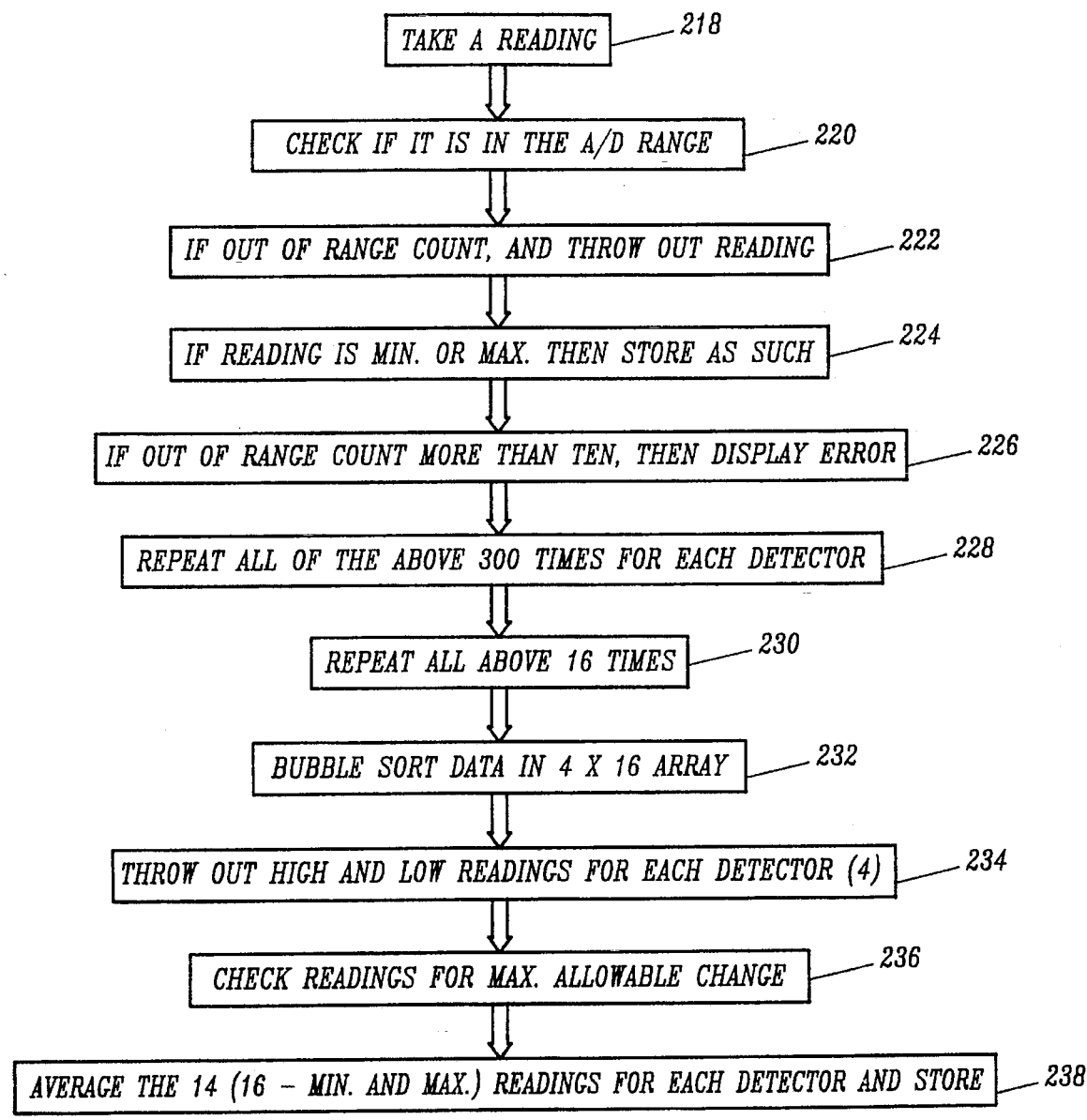
FIG. 11 is a flow chart of the GET_DATA subroutine called from the processes of the main operation process illustrated in FIG. 5.

There is shown in FIG. 7 a flow chart showing the steps involved in warm-up/air calibration process 134. In block 156, one of the LEDs 46, designating that a "purge" is taking place, is turned on. At the same time LCD display screen 48 displays "COLD" to indicate that a warm-up is taking place. In block 158 a 90 second delay is set prior to beginning the purge operation in block 160. In block 160, pump 72 is turned on to begin purging system 10. LCD display 48 displays the text "CAL" to indicate calibration is taking place. A ten second timer is set in block 162 prior to beginning GET_DATA subroutine 216 (FIG. 11). Following execution of GET_DATA subroutine 216, processing moves to block 164 where a check is made against the data from the air calibration. In block 166, if the air calibration is valid, the air calibrations values are stored. If they are not valid, GET_DATA subroutine 216 is repeated up to a maximum of three times in an exemplary embodiment. If valid air calibration results are not obtained after three attempts, an error code is displayed on LCD display 48 and a "FAULT" LED in LED panel 46 is turned on.

Figure 8:
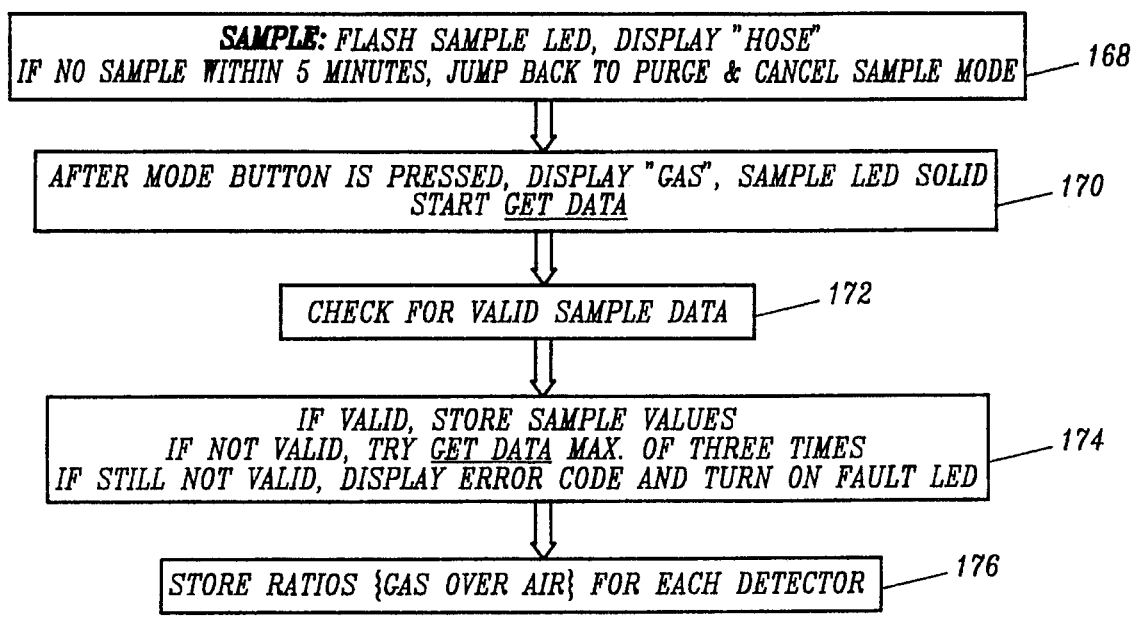

There shown in FIG. 8 a flow chart for sample process 136. Sample process 136 begins at block 168 where the "SAMPLE" LED is flashed while LCD display 48 displays the text "HOSE". If a refrigerant sample 14 is not input through input port 17 within 5 minutes and the "ENTER" button 40 has not been depressed, processing moves back to block 156 of FIG. 7 to repeat the purge. At this time sample process 136 is cancelled. In block 170, if the enter button in keypad 40 is pressed, LCD display 48 displays the text "GAS" and the sample LED is constantly illuminated (not flashing). GET_DATA subroutine 216 is also started. In block 172, a check is made to determine whether sample data received is valid. If sample data is valid, the sample values are stored in memory 116 (FIG. 4). If not valid, GET_DATA subroutine 216 is repeated up to three times. After three attempts, if a valid sample data is not received, an error message is displayed on LCD display 48 and fault LED is lit. If valid sample data is received, In block 176, the ratios of refrigerant gas 14 over air is determined for each detector.

Figure 9:
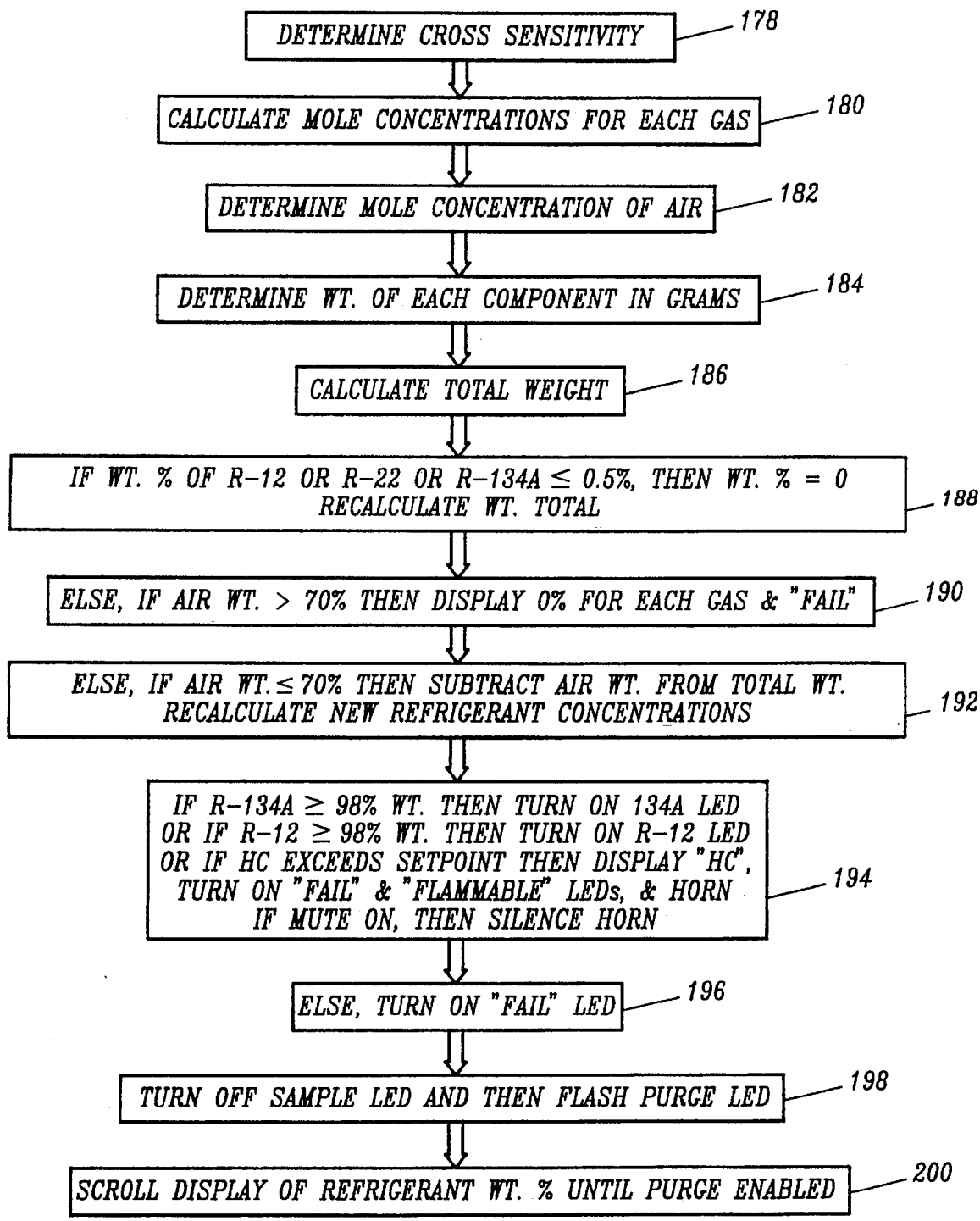

There shown in FIG. 9 a flow chart for identification process 138. Identification process 138 begins by determining the cross sensitivity of the electrical output signals of sensors 30A–30D in block 178. Following the cross sensitivity examination, the mole concentration for each refrigerant and hydrocarbon gas detected is calculated in block 180 accounting for cross sensitivity determined in block 178. The mole concentration of air is determined in block 182. Following the mole concentration calculations, the weight of each component (each refrigerant and hydrocarbon gas and air) is determined in grams for calculation purposes. In block 186, the total weight of refrigerant gases is calculated.

In blocks 188, 190, 192 and 194, various weight calculations pertaining to the exemplary embodiment are carried out. The weight calculations determine the percentage of refrigerants identified in this process. In block 188, if a refrigerant gas other than a hydrocarbon has a weight percentage of less than 0.5% then the weight percentage of that gas is considered to be 0 (zero) and the total weight is recalculated. In block 190, if the weight of air is greater than 70% of the total then the gas weights are set at 0 (zero) for each refrigerant gas and the text "FAIL" is displayed on LCD display 48. In block 192 if the weight of air is less than or equal to 70% of the total weight, then the air weight is subtracted from the total weight and the refrigerant gas concentrations are recalculated. This block assumes that if the air weight is less than or equal to 70%, then a sufficient gas sample has been identified. In block 194, determinations are made regarding the weight percentage of R134A and R12. If either of these gases are greater than or equal to 98% then a particular LED 46 is turned on, representing that one of these gases accounts for 98% or greater of the refrigerant gas being sampled. If a hydrocarbon exceeds a set threshold level then the text "HC" is displayed on LCD display 48, the "FAIL" and "FLAMMABLE" LEDs are turned on and an external horn (not shown) is sounded. If a mute button on keypad 40 has been depressed, then the horn is silenced. If the conditions in blocks 190, 192 and 194 are not met the "FAIL" LED 46 is turned on in block 196. This indicates that the sample is not a 98% or greater pure sample. In block 198 the "SAMPLE" LED is turned off and the "PURGE" LED is flashed. In block 200, the refrigerant gas weight percentages are displayed on LCD display 48 until purge is enabled.

Figure 10:
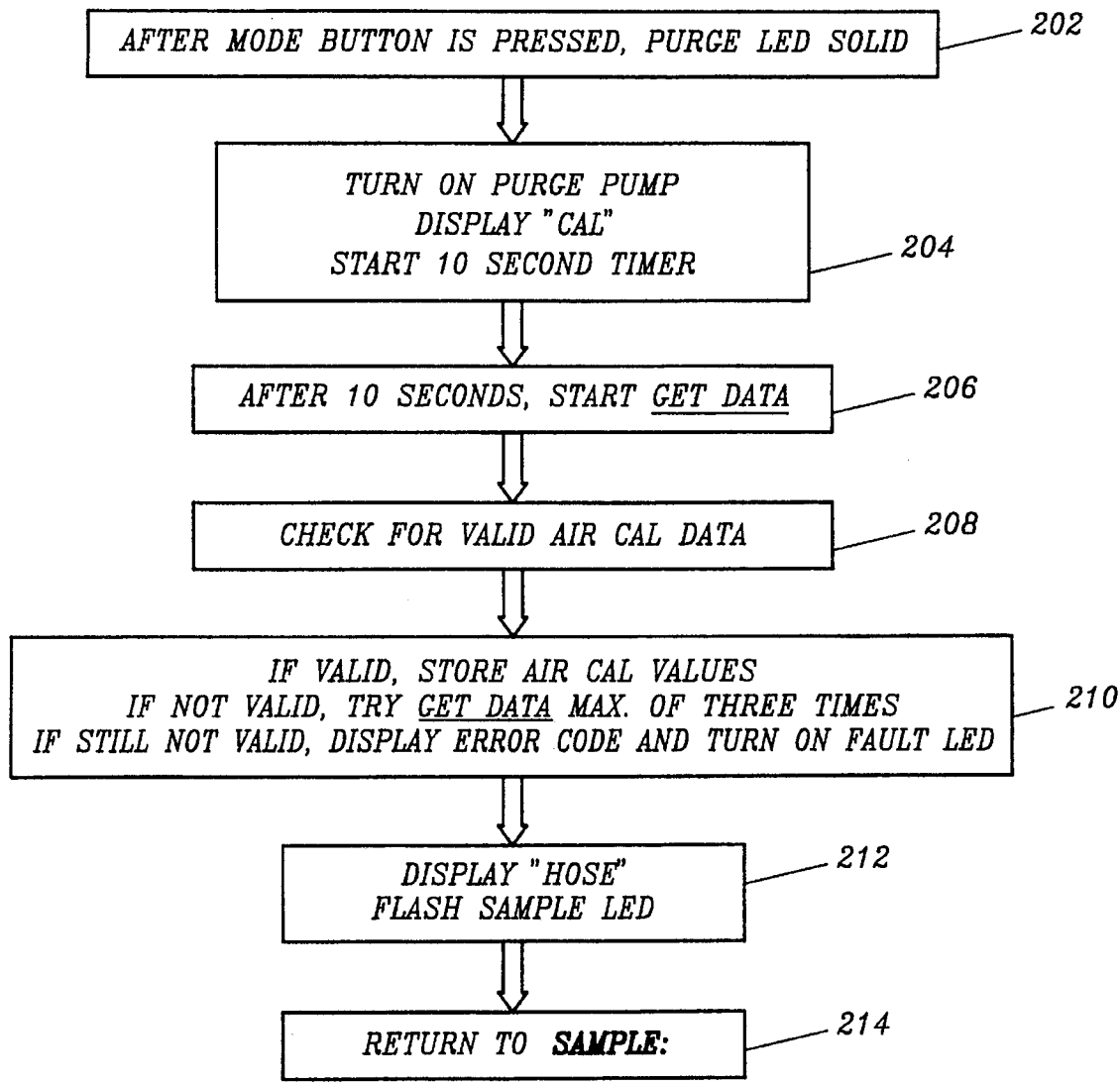

There shown in FIG. 10 purge air calibration process 140. Purge/air calibration process 140 begins at block 202 where the "PURGE" LED is constantly illuminated (not flashing) after the enter button in keypad 40 is pressed. Purge pump 72 is turned on in block 204 and the text "CAL" is displayed on LCD display 48. A timer is started prior to beginning GET_DATA subroutine 216 in block 206. Valid air calibration data is checked in block 208 and if valid, air calibration values are stored in block 210. If the air calibration values are not valid, the GET_DATA subroutine 216 is repeated up to three times. If valid air calibration values are not obtained during the three attempts, an error code is displayed on LCD display 48 and "FAULT" LED 46 is turned on. In block 212, the "SAMPLE" LED is flashed and the text "HOSE" is displayed on LCD display 48 indicating that a sample should be input into system 10. In block 214 processing returns to block 168 of FIG. 8.

There shown in FIG. 11 a flow chart of the GET_DATA subroutine 216. GET_DATA subroutine 216 is used to determine the peak to peak value of the four independent positive 3 Hz DC sine wave conditioned signals from detectors 30A–30D. In an exemplary embodiment the method involves taking multiple readings over slightly one period to ensure both peaks have been sampled. In an exemplary embodiment this process is then repeated multiple times for each of the four detector signals.

In block 218, a reading from each detector 30A–30D is taken. In block 220, it is determined if the reading is in the range for the analog to digital convertor being used. In block 222, a determination is made if the count is outside of the range. In block 224, the reading is stored if it is a minimum or maximum value. In block 226, if an out of range counter is more than 10, an error message is displayed on LCD display 48. Steps 218 to 226 are repeated multiple times for detectors 30A–30D in an exemplary embodiment. In block 230, steps 218 to 228 are repeated multiple times in an exemplary embodiment of the present invention. In block 232 a bubble sort of the data takes place in a 4×16 array. The high and low readings for each of the four detectors 30A–30D are set aside in block 234. The readings are then checked for a maximum allowable change in block 236. In block 236 the readings are verified to have less than 0.5% span for each detector 30A–30D. The remaining readings for each detector 30A–30D are stored in memory 116.

Figure 12A:
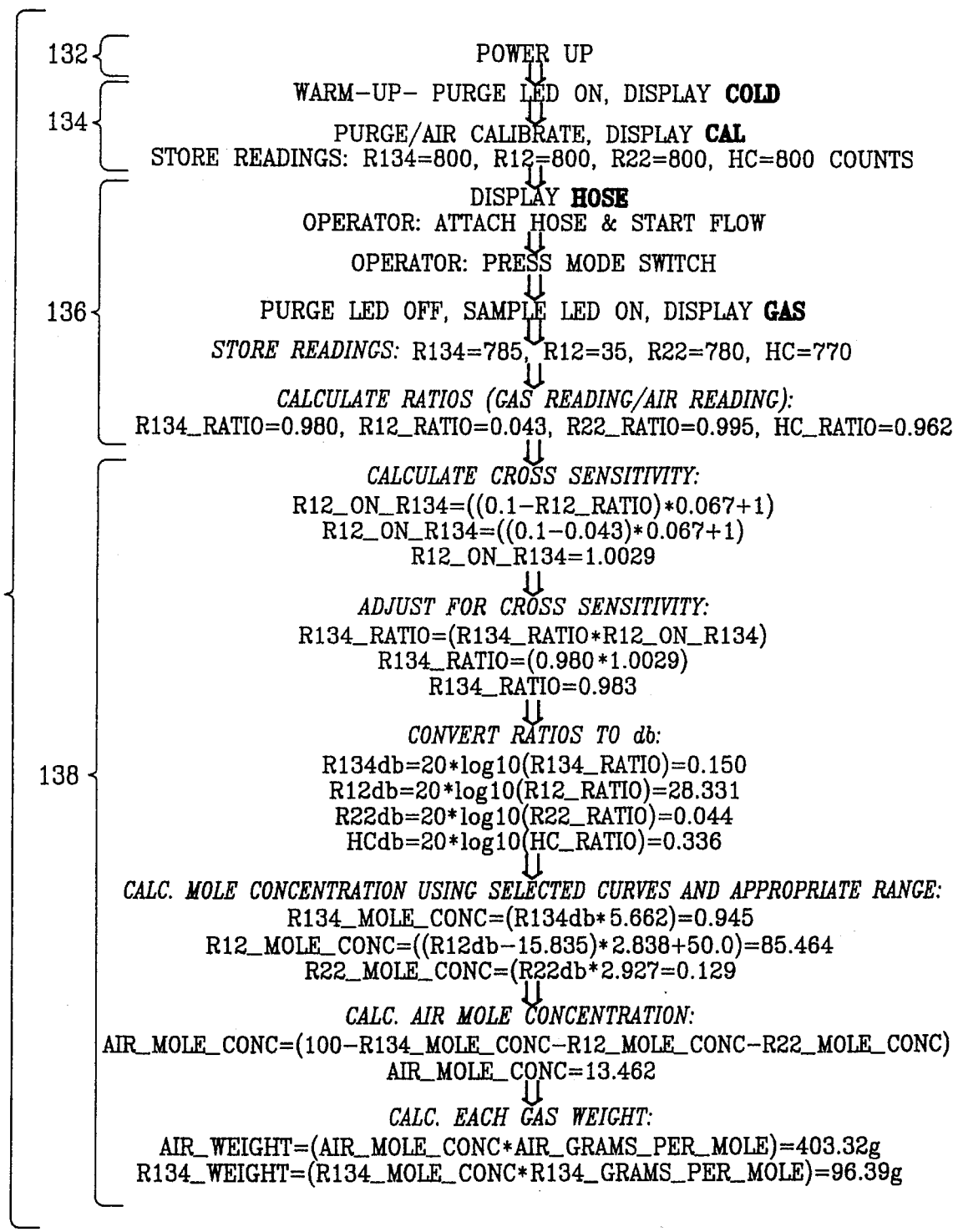

There shown in FIG. 12 a flow chart of an example run of system 10 corresponding to the process shown in flow chart 130. For the example shown in FIG. 12, a refrigerant sample with a vapor mixture of 99.07% R12 and 0.924% R134A was tested.

Processing begins by power up and warm-up using process routines 132 and 134. During the air calibration stage of process 134, various readings are stored. These are R134 (short hand version for R134A)=800, R12=800, R22=800 and HC (short hand for hydrocarbon)=800. Next, in sample process 136, the operator attaches hose 16 in response to the text display on LCD display 48 "HOSE" and the flashing "SAMPLE" LED 46. The operator then presses the enter switch on keypad 40 to begin operation. Output electrical signals from detectors 30A–30D are read, following the elimination of refrigerant gas 14. For this example, the R134A reading is 785, the R12 reading is 35, the R22 reading is 780 and the hydrocarbon reading is 770. Ratios for each of these gases over air are then calculated.

Next, identification process 138 begins by calculating the cross-sensitivity of the respective refrigerant gases for each detector. Next an adjustment for cross-sensitivity is made based on the calculation. The ratios of gas over air are then converted to decibels (dB). Mole concentrations for each gas are calculated using prestored and manufacturer selected equations derived from mole % versus dB detector response output curves FIGS. 15A–15D for each detector 30A–30D. Following the mole concentration calculation for the particular gases, the air mole concentration is calculated. Next the gas weight is calculated and then the total weight. Following the weight calculations, the percent concentration for each refrigerant gas is calculated. For this example, R22 weight is set to zero because its concentration is less than 0.5%. The air weight for this example has been determined to be less than 70% of the entire refrigerant, so air is removed from the total weight and a new R22 weight (which previously was set to zero) is calculated. Next the percent calculations for each gas are recalculated with the result R12 is greater than 98% of the refrigerant. This result is displayed by turning on the R12 LED and scrolling the display of the respective weights.

Air calibration process 140 then begins following the pressing of enter switch on keypad 40.

Commercial Refrigerant Gas Identifier

The present invention also functions as a commercial refrigerant identifier using a "fingerprint" method of identification. The fingerprint method involves identifying a commercial refrigerant by unique set of outputs from the four detectors 30A–30D received following infrared illumination of a commercial refrigerant by light from infrared light source 26. For the automotive example, each of the four detectors 30A–30D is tuned with a filter 32A–32D to a respective automotive refrigerant. As the number of commercial refrigerants can range from approximately 25–35 different types, a similar identification process to that used for automotive refrigerants would require from 25 to 35 detectors, assuming a different detection wavelength range for each of the commercial refrigerants. Therefore, the "fingerprint" method of identification is employed to reduce the required number of detectors.

The four points on the infrared spectra for which the filters 32A–32D are designed to detect, cover a broad range of the infrared spectra, namely 3.14 microns for hydrocarbons, 10.3 microns for R134A, 11.3 microns for R12 and 12.5 microns for R22. Most commercial refrigerants absorb infrared light within these ranges of absorption. By recording the signal outputs of the four detectors 30A–30D when exposed to gas absorbed infrared light following illumination of a commercial refrigerant with infrared light from light source 26, a unique fingerprint or signature can be observed in many cases. This fingerprint is comprised of the separate readings from the four detectors 30A–30D. Thus, when undergoing commercial refrigerant analysis, detectors 30A–30D no longer have individual significance for a particular refrigerant, but, rather, the four detectors in combination will provide a unique response for each commercial refrigerant.

For example, unknown refrigerant gas 14 may be sampled and attenuation readings in the 10.3 microns and 11.3 microns wavelength regions are output by 2 of the detectors. This does not necessarily mean that the unknown refrigerant contains R134A and R12 as could be the case for the automotive refrigerant identifier example previously described. It instead indicates that the sampled gas is absorbed in these two regions of the infrared spectra. If a library of fingerprints/signatures for refrigerant gases is maintained, the actual readings from the outputs of the detectors can be compared against the library to identify the unknown refrigerant 14 sample. Further, it is possible to store the signature/fingerprints of slightly contaminated refrigerants to help quantify the purity of a refrigerant gas sample being tested. Because of the different information resulting from a fingerprint identification, as compared to an individual detector identification (for automotive refrigerants as described above) the output LEDs 46 and keypad 40 may require different information and/or a different configuration than that shown in FIG. 2. Appropriate information and/or configuration would be understood by those skilled in the art.

Because of the number of commercial refrigerants in use, and the likelihood of a particular refrigerant system having a limited number of possible refrigerants in use, identification could be limited to specific groups of refrigerants which are most likely or more likely to be used for a particular refrigeration market or application. If the case arose that two or more refrigerants which could possibly be within a sample have an identical or similar fingerprint, then a detection of that particular fingerprint would result in a display that further testing is required to identify the particular refrigerant.

In running the process for fingerprint identification of refrigerant gases, process steps 132, 134, 136, 140 and 142 shown in FIG. 5 and the corresponding more-detailed flow diagrams, shown in FIG. 14, can be used for fingerprint identification as well. Differences in some of these routines would correspond to fingerprint analysis such as changes in LED 46 designations and possibly differences in keypad 40 buttons. In particular, it is the identification process which has substantial changes from that of identification process 138 shown in FIG. 9.

Figure 13:
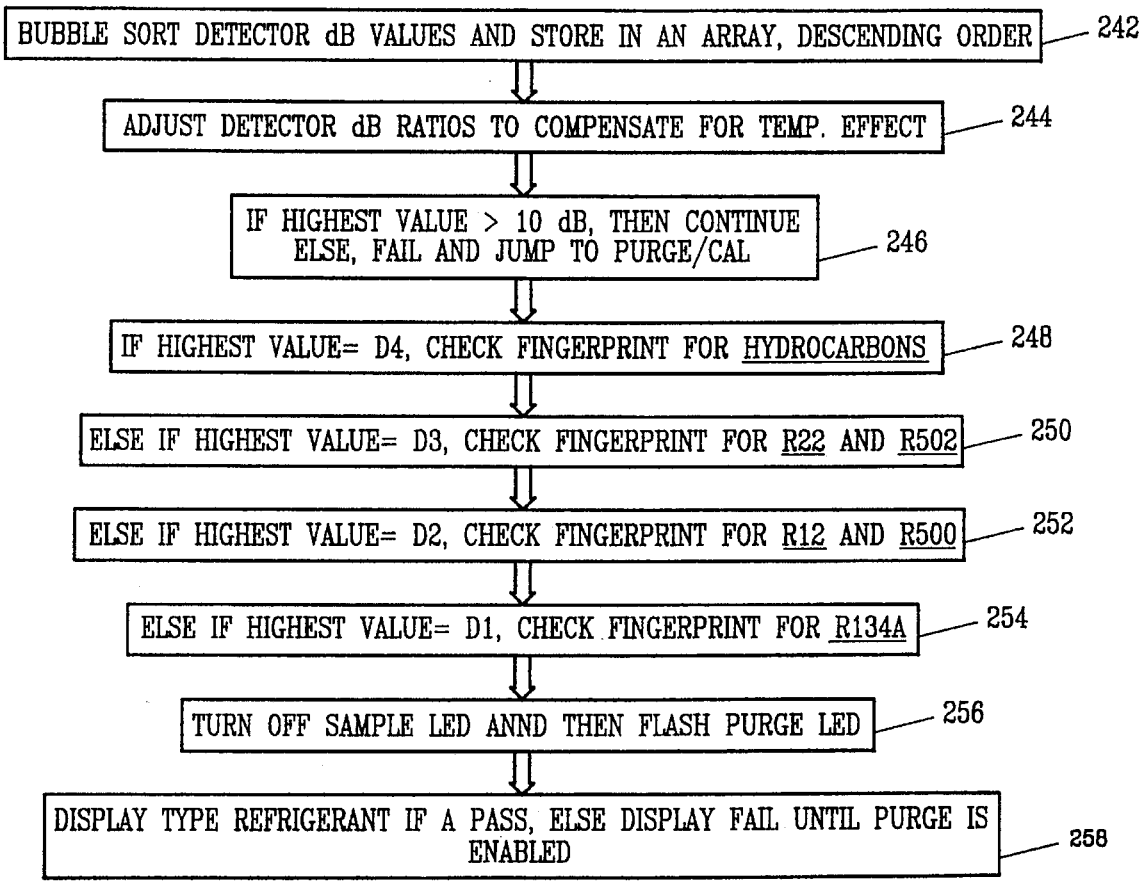
FIGS. 13 and 14A–14C are flow charts showing operation of an exemplary refrigerant identification system identifying specific commercial refrigerants.

There shown in FIG. 13, a flow chart for a fingerprint identification process 246. Fingerprint identification process 246 begins by bubble sorting the detector decibel values and storing them in an array in block 242. The detector decibel ratios are then adjusted to compensate for any temperature effects. Next, as long as the highest value is above 10 decibels, processing continues. In block 248, the highest value is compared against a predetermined value shown as "D4" in block 248. If true, processing moves to FIG. 14 where the hydrocarbon fingerprint flow chart 248 is entered. Block 250, 252 and 254 compare the highest value against predetermined values for R22, R502, and R12/R500, respectively. Of course, predetermined values for other refrigerants could be tested at this time. In block 256, sample identification is complete and the sample LED is turned off and the purge LED is flashed. In block 258, the type of refrigerant identified is displayed on LCD display 48 if a refrigerant has been identified. If not, a fail indication is displayed.

Figure 14A:
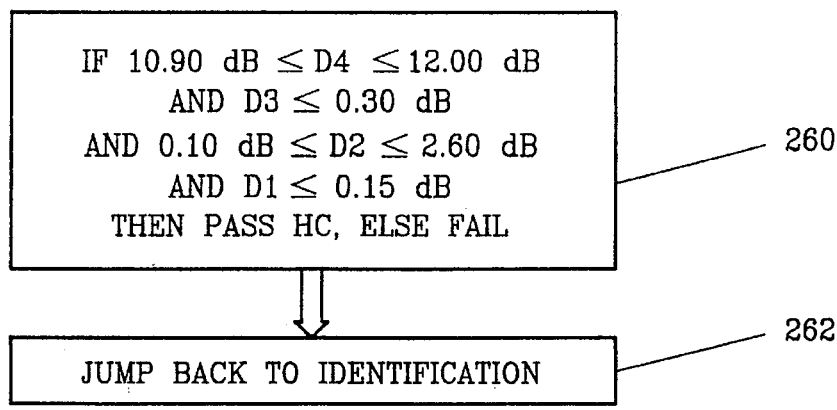
Figure 14B:
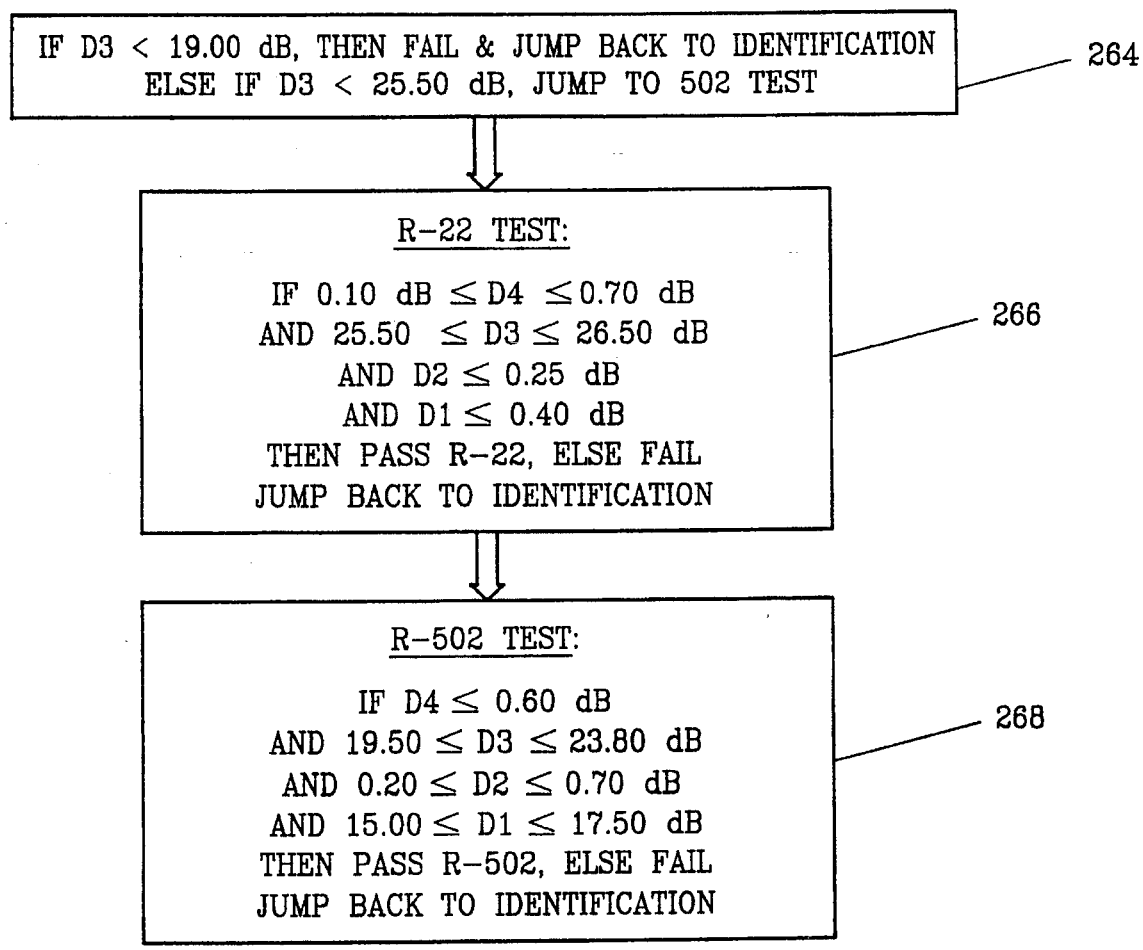
Figure 14C:
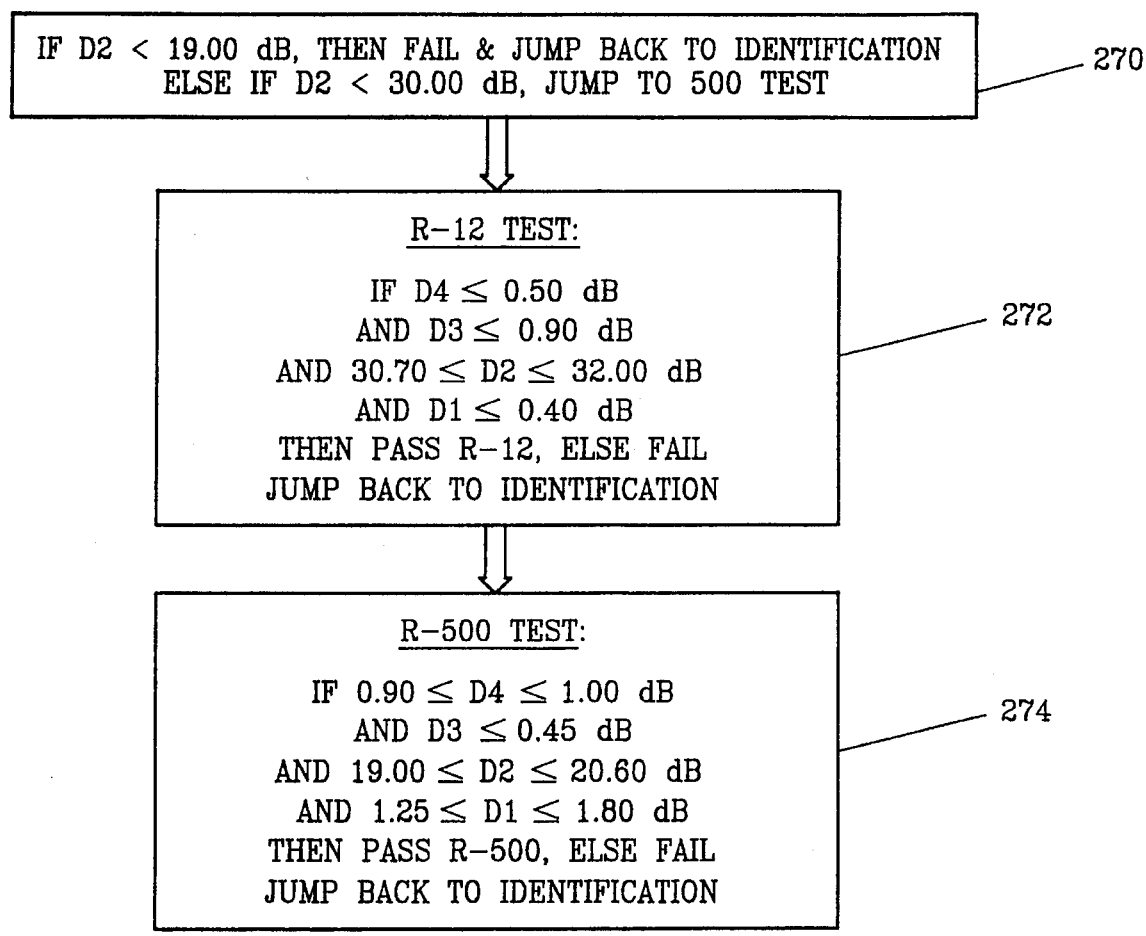
Figure 15A:
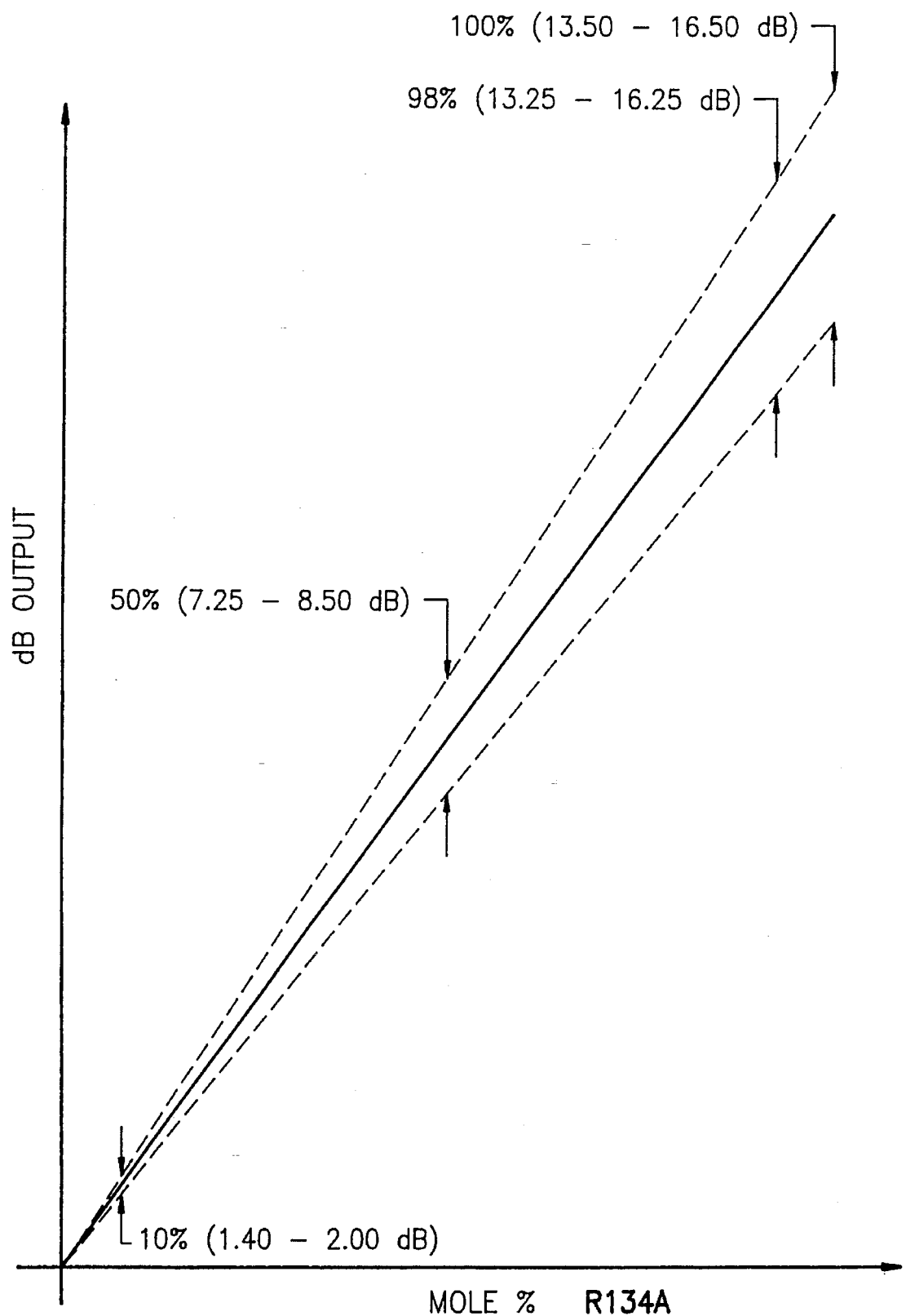
FIGS. 15A–15D are exemplary graphs used in calibrating devices manufactured in accordance with the present invention.
Figure 15B:
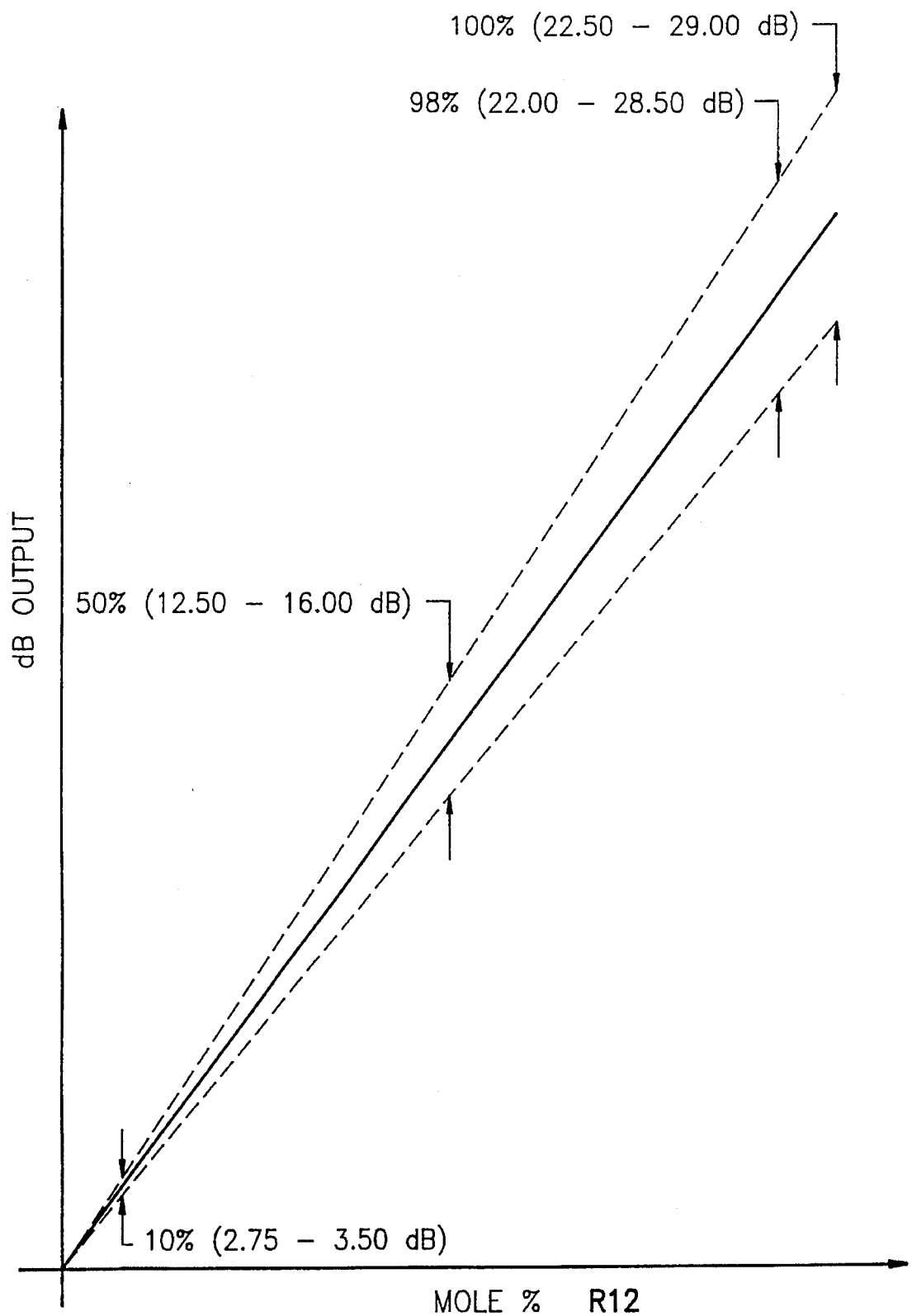
Figure 15C:
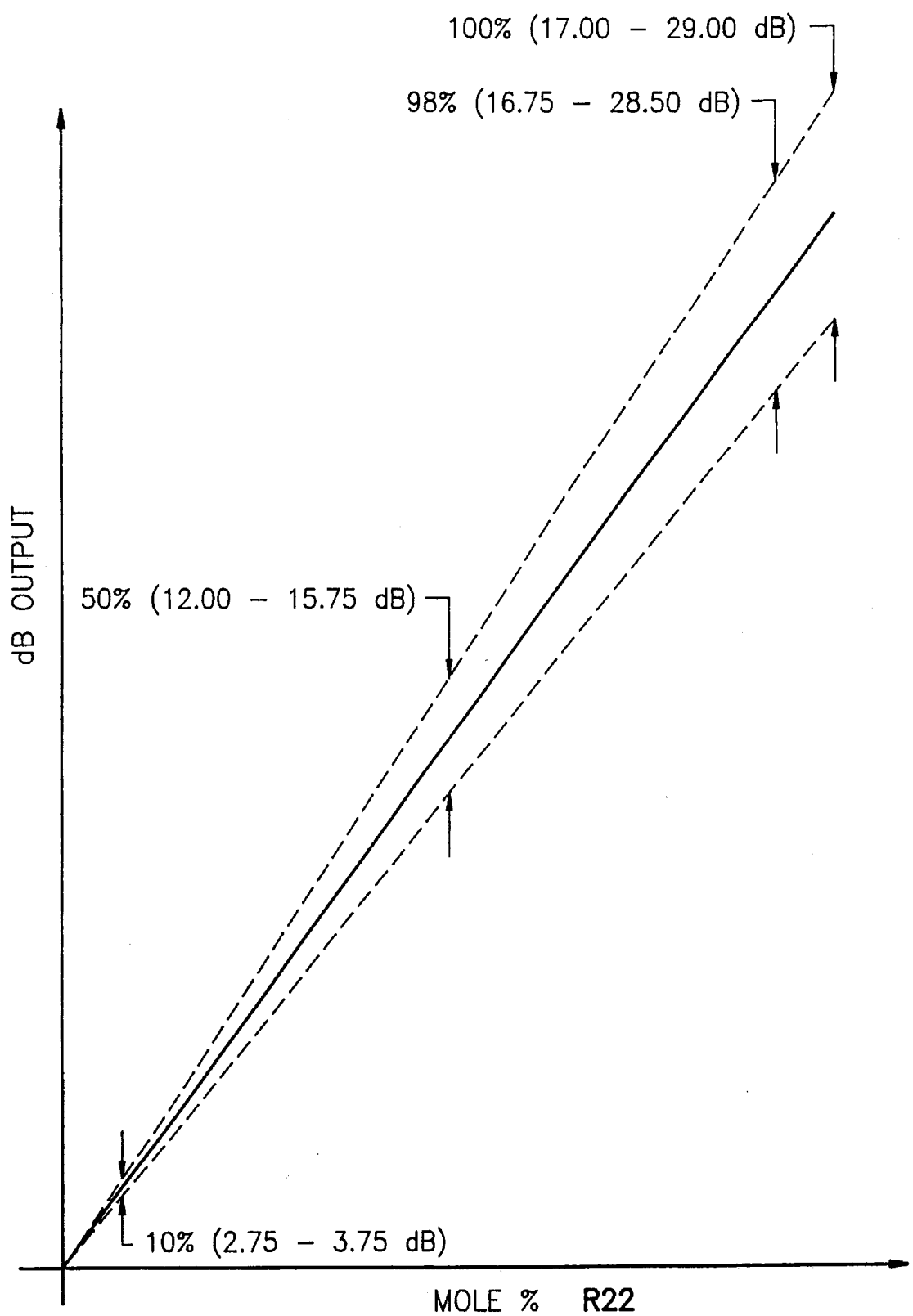
Figure 15D:
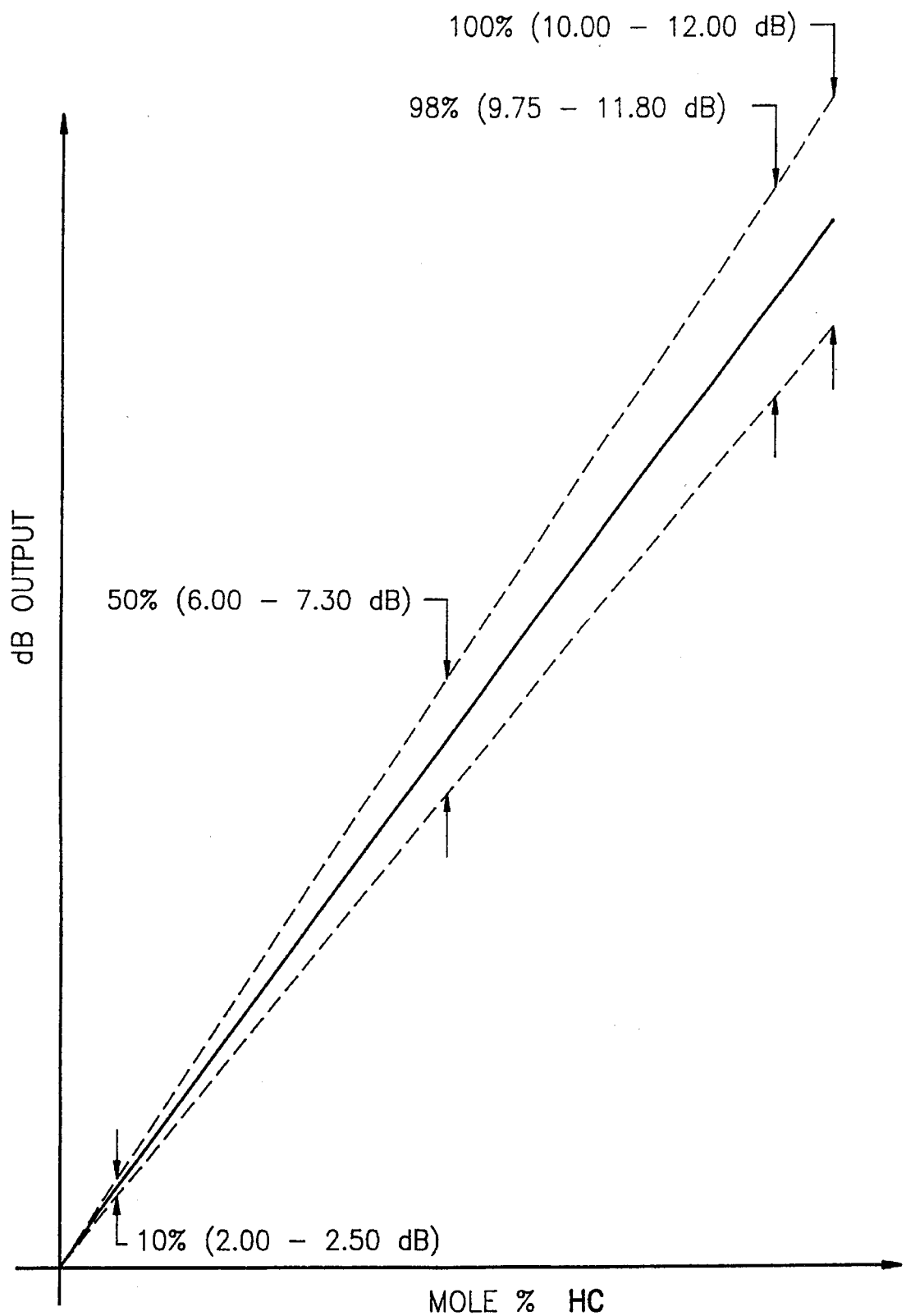

FIGS. 14A–14C show respective analysis for detection of hydrocarbons, R22/R502, and R12/R500 refrigerants as an example of the fingerprint identification system/method.

Fingerprints for other refrigerant gases could be stored and appropriate logic implemented to compare actual values from detectors 30A–30D for identification of particular refrigerants.

While particular embodiments of the present invention are disclosed herein, it is not intended to limit the invention to such disclosure, and changes and modifications may be incorporated and embodied within the scope of the following claims:

What is claimed:

1. A system for determining the presence of at least two vapors in a refrigerant sample, comprising:

a) an infrared light source;

b) at least two infrared detectors, each sensitive to a different predetermined wavelength range of infrared light, positioned to receive infrared light emitted from said infrared light source and each adapted to output an electrical signal corresponding to:
   intensity of infrared light received in each respective predetermined wavelength range;

c) a test area for containing said refrigerant sample and disposed between said infrared light source and said infrared detectors, wherein said infrared light emitted from said infrared light source can pass through said refrigerant sample contained in said test area prior to reception by said infrared detectors;

d) input means for inputting said refrigerant sample into said test area;

e) means for reading said separate electrical signals and determining whether said separate electrical output signals correspond to one or more of said at least two vapors;

f) means for determining an amount of air, if any, in said refrigerant sample, g) display means for displaying whether said refrigerant sample contains said one or more of said at least two vapors and said amount of air.

2. A system for determining the presence of at least two vapors in a refrigerant sample in accordance with claim 1, wherein said predetermined wavelength range of infrared light encompasses a resultant infrared light wavelength after infrared light from said infrared light source passes through a particular vapor.

3. A system for determining the presence of at least two vapors in a refrigerant sample in accordance with claim 1, comprising at least four infrared detectors, each sensitive to a different predetermined wavelength range of infrared light encompassing a resultant infrared light wavelength after infrared light from said infrared light source passes through a particular vapor.

4. A system for determining the presence of at least two vapors in a refrigerant sample in accordance with claim 3 wherein a separate one of said four infrared detectors is sensitive to infrared light passing through R12, R134a, R22 and hydrocarbon refrigerants, respectively.

5. A system for determining the presence of at least two vapors in accordance with claim 2, wherein said output electrical signal of said infrared detector has an amplitude corresponding to the percentage of said particular vapor contained in said refrigerant sample.

6. A system for determining the presence of at least two vapors in accordance with claim 1, further comprising means for subtracting said amount of air from said refrigerant sample, and wherein said output signal of said infrared detector has an amplitude corresponding to the percentage of said particular vapor contained in said refrigerant sample after subtracting said amount of air from said refrigerant sample.

7. A system for determining the presence of at least two vapors in accordance with claim 1, further comprising means for purging said system of gas, prior to the input of said refrigerant sample.

8. A system for determining the presence and quantity of at least two vapors in a refrigerant sample, comprising:
   a) an infrared light source;
   b) four infrared detectors,
      i) each sensitive to a different predetermined wavelength range of infrared light encompassing a resultant infrared light wavelength after infrared light from said infrared light source passes through a particular vapor,
         wherein a separate one of said four infrared detectors is sensitive to infrared light passing through R12, R134a, R22 and hydrocarbon refrigerants, respectively, and
      ii) each adapted to output an electrical signal corresponding to any infrared light received in said predetermined wavelength range for said separate one of said four infrared detectors,
         wherein said output electrical signal has an amplitude corresponding to the percentage of said particular vapor contained in said refrigerant sample;
   c) a test area for containing said refrigerant sample and disposed between said infrared light source and said infrared detector, wherein said infrared light emitted from said infrared light source can pass through said refrigerant sample contained in said test area prior to reception by said infrared detector;
   d) a hose, pressure regulator, and flow orifice for inputting said refrigerant sample into said test area at a predetermined pressure;
   e) a processor for reading said output electrical signal and determining (1) whether said output signal corresponds to one or more of said four said vapors and (2) whether air is present in said refrigerant sample;
   f) display means for displaying whether said refrigerant sample contains one or more of said four vapors and an indication of the quantity of said one or more of said four vapor present in said refrigerant sample.

9. A method for determining the presence of at least two vapors in a refrigerant sample comprising the steps of:
   a) producing a gas absorbed infrared light by illuminating said refrigerant sample with infrared light from an infrared light source;
   b) illuminating at least two infrared detectors with said gas absorbed infrared light;
   c) determining whether said gas absorbed infrared light is within a predetermined wavelength range and if said gas absorbed infrared light is within a predetermined wavelength range:
      i) outputting a signal corresponding to whether said gas absorbed infrared light is within said predetermined wavelength range,
      ii) determining whether said vapor is present in said refrigerant sample based on said output signal;
   d) determining whether air is present in said refrigerant sample, and
   e) displaying whether one or more of said at least two vapors and said air are present in said refrigerant sample.

10. A method for determining the presence of at least two vapors in a refrigerant sample in accordance with claim 9, wherein step (b) comprises:

illuminating four infrared detectors with said gas absorbed infrared light, each of said four infrared detectors sensitive to a different predetermined wavelength range of infrared light encompassing a resultant infrared light wavelength after infrared light from said infrared light source passes through a particular vapor.

11. A method for determining the presence of at least two vapors in a refrigerant sample in accordance with claim 10, wherein a separate one of said four infrared detectors is sensitive to infrared light passing through R12, R134a, R22 and hydrocarbon refrigerants, respectively.

12. A method for determining the presence of at least two vapors in a refrigerant sample in accordance with claim 10, wherein step (c) (i) comprises:
   each separate one of said four infrared detectors outputting a separate electrical signal corresponding to infrared light received in said predetermined wavelength range for said separate one of said four infrared detectors.

13. A method for determining the presence of at least two vapors in a refrigerant sample in accordance with claim 9, comprising the further step of determining the amount of air present in said refrigerant sample.

14. A method for determining the presence of at least two vapors in a refrigerant sample in accordance with claim 9, comprising the further step of outputting a separate signal from each of said four infrared detectors, corresponding to the percentage of said particular vapor contained in said refrigerant sample.

15. A method for determining the presence of at least two vapors in a refrigerant sample in accordance with claim 9, comprising the further step of purging said system of gas, prior to the input of said refrigerant sample.

16. A method for determining the presence and quantity of at least two vapors in a refrigerant sample comprising the steps of:
   a) producing a gas absorbed infrared light by illuminating said refrigerant sample with infrared light from an infrared light source;
   b) illuminating four infrared detectors with said gas absorbed infrared light, each of said four infrared detectors sensitive to a different predetermined wavelength range of infrared light encompassing a resultant infrared light wavelength after infrared light from said infrared light source passes through a particular one of said at least two vapors,
      wherein a separate one of said four infrared detectors is sensitive to infrared light passing through R12, R134a, R22 and hydrocarbon refrigerants, respectively;
   c) each of said four infrared detectors outputting a signal corresponding to whether said gas absorbed infrared light is within said predetermined wavelength range for said separate one of said four infrared detectors,
      wherein said respective output electrical signals have an amplitude corresponding to the percentage of said particular vapor contained is said refrigerant sample;
   d) determining whether one or more of said at least two vapors is present in said refrigerant sample based on said respective output signals;
   e) determining whether air is present in said refrigerant sample; and
   f) displaying whether one of more of said at least two vapors and said air are present in said refrigerant sample and an indication of the quantity of said one or more of said vapors present in said refrigerant sample.

* * * * *